US009289122B2

(12) United States Patent
Chinnock et al.

(10) Patent No.: US 9,289,122 B2
(45) Date of Patent: Mar. 22, 2016

(54) PORTABLE RETINAL CAMERA AND IMAGE ACQUISITION METHOD

(71) Applicant: Optimum Technologies, Inc., Southbridge, MA (US)

(72) Inventors: Randal B. Chinnock, Southbridge, MA (US); Frederick G. Bargoot, Wellesley, MA (US); George Grubner, Needham, MA (US); Jason P. Julian, Rutland, MA (US); Sarah Latta, Worcester, MA (US); William Weber, Olivebridge, NY (US)

(73) Assignee: Optimum Technologies, Inc., Southbridge, MA (US)

( * ) Notice: Subject to any disclaimer, the term of this patent is extended or adjusted under 35 U.S.C. 154(b) by 645 days.

(21) Appl. No.: 13/645,763

(22) Filed: Oct. 5, 2012

(65) Prior Publication Data
US 2013/0033593 A1    Feb. 7, 2013

Related U.S. Application Data

(63) Continuation of application No. PCT/US2010/052761, filed on Oct. 14, 2010.

(60) Provisional application No. 61/251,326, filed on Oct. 14, 2009.

(51) Int. Cl.
    *H04N 7/18* (2006.01)
    *A61B 3/14* (2006.01)
(52) U.S. Cl.
    CPC ....................................... *A61B 3/14* (2013.01)
(58) Field of Classification Search
    CPC .......................................................... A61B 3/14
    USPC ........................................................... 348/78
    See application file for complete search history.

(56) References Cited

U.S. PATENT DOCUMENTS

2003/0025876 A1    2/2003  Nanjo
2006/0146284 A1*   7/2006  Collins et al. ................. 351/215
(Continued)

FOREIGN PATENT DOCUMENTS

EP       1 543 767 A1    6/2005
EP       2 184 006 A1    5/2010
WO   WO 2007/030450 A2   3/2007

OTHER PUBLICATIONS

International Search Report issued in priority PCT application No. PCT/US2010/052761 mailed May 9, 2011.
International Preliminary Report on Patentability issued in priority PCT application No. PCT/US2010/052761 mailed Apr. 17, 2012.

*Primary Examiner* — Yulin Sun
(74) *Attorney, Agent, or Firm* — Brian M. Dingman; Dingman, McInnes & McLane, LLP

(57) ABSTRACT

A camera for capturing an image of an object, for example an eye. The camera has at least two light sources and an image-sensing system having two image sensors. A multiple branch optical system transmits outgoing light from the light sources to the object, and transmits incoming light from the object to the image-sensing system. The multiple branch optical system includes an autofocusing element such as a variable power optical element that varies the focus of the incoming light. There is also an image display. There is a controller that controls the operation of the light sources, controls acquisition of images by the image-sensing system, and controls the display of images on the image display. The controller activates an autofocus light source and uses the resulting captured image to automatically adjust the image exposure parameters. The controller automatically adjusts the autofocusing element to improve the image focus, and then activates the second light source and acquires one or more images of the object while the second light source is activated.

31 Claims, 16 Drawing Sheets

(56) References Cited

U.S. PATENT DOCUMENTS

| | | | |
|---|---|---|---|
| 2006/0269261 A1* | 11/2006 | Wernersson | 396/55 |
| 2007/0030450 A1* | 2/2007 | Liang et al. | 351/206 |
| 2007/0146535 A1 | 6/2007 | Nanjo | |
| 2007/0285793 A1* | 12/2007 | Liu et al. | 359/630 |
| 2007/0291230 A1 | 12/2007 | Yamaguchi et al. | |
| 2008/0212029 A1* | 9/2008 | Ichikawa | 351/208 |
| 2008/0259274 A1* | 10/2008 | Chinnock | 351/206 |

\* cited by examiner

PORTABLE RETINAL CAMERA AND IMAGE ACQUISITION METHOD

CROSS REFERENCE TO RELATED APPLICATION

This application is a continuation of PCT Patent Application PCT/US2010/052761 filed on Oct. 14, 2010. Priority is claimed. This application also claims priority of Provisional Patent Application Ser. No. 61/251,326 filed on Oct. 14, 2009. Both priority applications are hereby incorporated herein by reference.

BACKGROUND

The present invention generally relates to the field of retinal imaging. Retinal imaging, as used in this application, refers to illuminating the human retina with non harmful visible or near infra-red (NIR) light, viewing the retina, and (optionally) capturing one or more images. The simplest retinal imaging device is the indirect ophthalmoscope. This device includes a low power white (broadband visible) light source and an optical system that includes an ocular. The instrument is placed between the patient's eye and the practitioner's eye, the patient's retina is illuminated, and the image of the patient's retina is transferred to the practitioner's retina. This type of screening examination is typically performed by primary care physicians. Indirect ophthalmoscopes have limited diagnostic capabilities, and do not have means for recording images, so if the screening exam indicates pathology, the patient is generally referred to an eye specialist (ophthalmologist or optometrist) for an examination with a more sophistical retinal imaging device that incorporates an electronic imaging device such as a CCD or CMOS camera, along with an image recording and archiving system. These retinal imaging devices are known as either "retinal cameras" or "fundus cameras". "Fundus" refers to the back of the eye. Typically retinal cameras and fundus cameras are large (table-top sized) and expensive and are used almost exclusively by eye specialists.

Retinal exams are used to visually screen for retinal abnormalities and to monitor the progression of known pathologies. Pathologies of the retina include malignancies, retinal detachment, age-related macular degeneration, retinitis pigmentosa, retinal infections, and diabetic retinopathy. Diabetic retinopathy is the leading cause of blindness in the world and with the rapid increase in the incidence and prevalence of diabetes, blindness from diabetes is a rapidly growing problem. If diagnosed early enough and treated appropriately (drugs are quite effective), blindness is generally preventable. Unfortunately, in the U.S. many people do not have access to eye specialists. This may result from poor compliance, lack of transportation to distantly-located eye specialists, or from reduced mobility due to obesity or other diabetic pathologies. The problem is more severe in many other parts of the world where health services are even less accessible than they are in the U.S. There is therefore great interest by health services organizations and governments around the world in means to increase access to diagnostic retinal imaging services.

SUMMARY

There is, therefore, an unmet need for a truly portable (e.g., compact, light weight, battery powered) retinal camera. This means that "the camera can be taken to the patient" rather than "the patient being taken to the camera". A second need is for the device to operate without the need for dilation of the patient's pupils. This is referred to as "non-mydriatic" use. Most practitioner office-based retinal cameras require that the pupils be dilated in order to introduce adequate illumination to the retinal area for image acquisition. In the U.S. and other countries, ocular dilating drops (usually atropine sulfate) must be administered by a physician. A retinal camera that may be used non-mydriatically will not require the presence of a physician or use of the pupil-dilating drops, so eye exams may be performed by visiting nurses, health-maintenance technicians, and other practitioners with limited training. A third need is for a portable, hand-held retinal camera with simple-to-use (e.g., built-in) telecommunications capabilities. Once retinal images have been captured and stored in such a device's internal memory, they may be uploaded via cellular network, telephone line, or Internet connection to an expert reading center. At the center, retinal imaging experts may promptly interpret the images, send a diagnosis to the field practitioner or other party, and prescribe treatment. This telemedicine approach, sometimes referred to as "tele-ophthalmology", has the potential to greatly increase access to retinal screening without compromising diagnostic quality. It also offers the promise of lower examination costs, greatly reduced lifetime treatments costs, and improved health outcomes.

The present invention relates in general to an apparatus and method for acquiring images. More specifically the invention is an apparatus and method directed to, but not limited to, acquiring images of the retina and/or the ear canal. Generally, the preferred embodiment of the portable retinal camera is a dual-sensor digital camera in which one sensor is used to guide a user during the initial, manual alignment phases of the image acquisition process and a second sensor is used for actual retinal image acquisition. Images obtained with low intensity, red illumination of the retina by the second sensor are used to control a series of automatic alignment and fine focusing steps prior to the image capture phase of the process. When focus, alignment, and exposure requirements are all met the second camera captures a burst of high resolution, white illuminated images of the retina.

This disclosure features a camera for capturing an image of an object. The camera has a first light source, a second light source, an image-sensing system comprising at least a first image sensor, and a multiple branch optical system that transmits outgoing light from the first and second light sources to the object and transmits incoming light from the object to the image-sensing system. The multiple branch optical system comprises a variable power optical element that varies the focus of the incoming light, and an image display. There is a controller that controls the operation of the first and second light sources, controls acquisition of images by the image-sensing system, and controls the display of images on the image display. The controller activates the first light source and uses the resulting captured image to automatically adjust the image exposure parameters. The controller automatically adjusts the variable power optical element to improve the image focus, and then activates the second light source and acquires one or more images of the object while the second light source is activated.

The controller may further cause an acquired image to be displayed on the image display to allow coarse alignment of the camera with the object. The image-sensing system may further comprise a second image sensor, wherein at least one of the two image sensors is a high-resolution color sensor. The multiple branch optical system may define a first light path from the first light source to the object, a second light path from the second light source to the object, a third light path from the object to the first image sensor and a fourth light path from the object to the second image sensor, where none of the light paths are entirely coincident. The first light source may emit deep Ored or near infrared light. The first light source may comprise one or more LEDs. The second light source may comprise one or more LEDs that emit broadband visible light.

The object that is imaged by the camera may be the fundus of an eye. The optical system may separate the illumination and imaging light paths such that these two light paths do not overlap in the pupil plane of the eye. The optical system may comprise configurable masks to control how one or both of the illumination and the image light is passed through the pupil of the eye. The camera may further comprise a fixation target illuminator system comprising an optical projector with a fixation target light source, the fixation target illuminator system presenting a virtual image of a target to the eye. The fixation target illumination source may comprise a plurality of point light sources, one defining a center and others arranged at a variety of field points relative to the center. The fixation target light source may be one of: one or more point sources; an extended object; and an electro-optic display device. The multiple branch optical system may define a fixation target light path from the fixation target light source to the eye. The fixation target illuminator system may further comprise a variable focus element in the fixation target light path, to vary the apparent distance of the virtual image of the fixation target light source from the eye. The variable focus element may be electro-mechanically adjusted.

The variable power optical element may comprise an electro-optical lens with variable focal length, wherein the focal length is varied by varying a voltage applied to the lens. The camera may include a third light source. The third light source may illuminate the object directly without elements of the multiple branch optical system between the third light source and the object. The camera may further comprise a hand-held housing that contains the first and second light sources, the image sensor, the multiple branch optical system and the controller, wherein the image display is mounted to the housing so as to be visible from the outside, wherein the housing defines an image acquisition aperture on a patient-facing side of the housing through which the light from the first and second light sources passes and light from the eye passes to reach the image-sensing system, and wherein the third light source is mounted on the outside of the patient-facing side of the housing proximate the image acquisition aperture. The third light source may emit near infrared light. The first light source may emit deep red or near infrared light that is used by the controller to accomplish automatic focus. The second light source may comprise an LED that emits broadband visible light that is used to capture a high-resolution image of light that is diffusely reflected by the fundus. The light from the third light source may be used by the controller to assist with coarse image alignment.

The optical system may further comprise a polarizer for polarizing the light from at least one of the first and second light sources, and a polarizing beamsplitter for directing to an imaging sensor the orthogonally polarized component of the polarized light that is diffusely reflected from the object. The optical system may further comprise a light beam combiner that directs the light from the first and second light sources along substantially the same light path. The camera may further comprise a data communication system that transmits image data from the camera. The controller may assist with coarse image alignment using a focus estimation image processing algorithm that calculates a focus figure-of-merit and notifies the operator when the figure-of-merit exceeds a predetermined threshold.

The camera may further comprise a closed loop control system having image shift as an input, wherein the processor determines the magnitude and direction of frame shift from a nominal center and generates a control signal that is used to modify the optical system to move the image back toward the nominal center. The variable power optical element may comprise an electro-optical lens with variable focal length, wherein the focal length is varied by varying a voltage applied to the lens, and wherein this control signal comprises a differential voltage that is applied to the electro-optical lens. The multiple branch optical system may comprise an electronically-variable aperture stop in the path of incoming light to an image sensor, and the controller may further control the stop size to improve focus during coarse image alignment. The camera may further comprise at least one of a GPS receiver that indicates the location at which an image is captured and a device for determining the orientation of the camera when an image is captured.

Also featured is a camera for capturing an image of the fundus of a human eye, comprising a first light source that emits deep red or near infrared light, a second light source that comprises an LED that emits broadband visible light that is used to capture a high-resolution image of light that is diffusely reflected by the fundus, and a third light source that emits near infrared light. There is also a fixation target illuminator system comprising an optical projector with a fixation target light source, the fixation target illuminator system presenting a virtual image of a target to the eye, and further comprising a variable focus element in the fixation target light path to vary the apparent distance of the virtual image of the fixation target light source from the eye. The camera also has an image-sensing system comprising a first image sensor that may be monochrome and be of relatively low resolution and a second image sensor that is a color sensor of high resolution. There is a multiple branch optical system that transmits outgoing light from the first and second light sources to the eye and transmits incoming light from the eye to the image-sensing system, and defines a first light path from the first light source to the eye, a second light path from the second light source to the eye, a third light path from the eye to the first image sensor, a fourth light path from the eye to the second image sensor, and a fixation target light path from the fixation target light source to the eye. The multiple branch optical system comprises an electro-optical lens that effects a change in its focal length to vary the focus of the incoming light to the second image sensor; the focal length is varied by varying a voltage applied to the lens. The optical system further comprises a polarizer for polarizing the light from the second light source, a polarizing beamsplitter for directing to the second image sensor the orthogonally polarized component of the polarized light that is diffusely reflected from the fundus, and a light beam combiner that directs the light from the first and second light sources along substantially the same light path. The optical system separates the illumination and imaging light paths such that these two light paths do not overlap in the pupil plane of the eye. The camera also has an image display and a controller that controls the operation of the first, second and third light sources, controls the fixation target illuminator system, controls acquisition of images by the image-sensing system, and controls the display of images on the image display. The controller causes an acquired image to be displayed on the image display to allow coarse alignment of the camera with the eye, activates the first light source and uses the resulting captured image to automatically adjust the image exposure parameters, and automatically adjusts the variable power optical element to improve the image focus.

The controller then activates the second light source and acquires one or more images of the fundus while the second light source is activated. The light from the third light source is used by the controller to assist with coarse image alignment using a focus estimation image processing algorithm that calculates a focus figure-of-merit and notifies the operator when the figure-of-merit exceeds a predetermined threshold. There is also a data communication system that transmits image data from the camera or receives data and a hand-held housing that contains the first and second light sources, the fixation target illuminator system, the image sensor, the multiple branch optical system and the controller. The image display is mounted to the housing so as to be visible from the outside. The housing defines an image acquisition aperture on a patient-facing side of the housing through which the light from the first and second light sources passes and light from the eye passes to reach the image-sensing system. The third light source is mounted on the outside of the patient-facing side of the housing proximate the image acquisition aperture.

Further featured is a method of capturing an image of the fundus of the eye, comprising providing a camera comprising a first light source, a second light source, an image-sensing system comprising at least a first image sensor, a multiple branch optical system that transmits outgoing light from the first and second light sources to the eye, and transmits incoming light from the eye to the image-sensing system, the multiple branch optical system comprising a variable power optical element that varies the focus of the incoming light, an image display and a controller that controls the operation of the first and second light sources and controls acquisition of images by the image-sensing system and display of images on the image display. The method further includes the step of operating the controller to first activate the first light source and use the resulting captured image to automatically adjust the image exposure parameters and automatically adjust the variable power optical element to improve the image focus, and then activate the second light source and acquire one or more images of the fundus while the second light source is activated.

In the method, before the exposure adjustment and image focus the controller may be operated to cause the acquired image to be displayed on the image display to allow coarse alignment of the camera with the eye. Also, a third light source may be provided, and light from the third light source may be used by the controller to assist with coarse image alignment.

Also featured herein is a method of capturing an image of the fundus of the eye, comprising providing a camera comprising a first light source that emits deep red or near infrared light, a second light source that comprises an LED that emits broadband visible light that is used to capture a high-resolution image of light that is diffusely reflected by the fundus, and a third light source that emits near infrared light. The camera also has a fixation target illuminator system comprising an optical projector with a fixation target light source, the fixation target illuminator system presenting a virtual image of a target to the eye, and further comprising a variable focus element in the fixation target light path to vary the apparent distance of the virtual image of the fixation target light source from the eye. The camera has an image-sensing system comprising a first image sensor that may be monochrome and of relatively low resolution and a second image sensor that is a color sensor of high resolution. The camera also has a multiple branch optical system that transmits outgoing light from the first and second light sources to the eye and transmits incoming light from the eye to the image-sensing system, and defines a first light path from the first light source to the eye, a second light path from the second light source to the eye, a third light path from the eye to the first image sensor, a fourth light path from the eye to the second image sensor, and a fixation target light path from the fixation target light source to the eye. The multiple branch optical system comprises an electro-optical lens that effects a change in its focal length, to vary the focus of the incoming light to the second image sensor, wherein the focal length is varied by varying a voltage applied to the lens. The optical system further comprises a polarizer for polarizing the light from the second light source, a polarizing beamsplitter for directing to the second image sensor the orthogonally polarized component of the polarized light that is diffusely reflected from the fundus, and a light beam combiner that directs the light from the first and second light sources along substantially the same light path, wherein the optical system separates the illumination and imaging light paths such that these two light paths do not overlap in the pupil plane of the eye. The camera further includes an image display and a controller that controls the operation of the first, second and third light sources, controls the fixation target illuminator system, controls acquisition of images by the image-sensing system, and controls the display of images on the image display. There is a data communication system that transmits image data from the camera or receives data, and a hand-held housing that contains the first and second light sources, the fixation target illuminator system, the image sensor, the multiple branch optical system and the controller. The image display is mounted to the housing so as to be visible from the outside. The housing defines an image acquisition aperture on a patient-facing side of the housing through which the light from the first and second light sources passes and light from the eye passes to reach the image-sensing system. The third light source is mounted on the outside of the patient-facing side of the housing proximate the image acquisition aperture. In the method, the controller is operated to first activate the third light source and cause an acquired image to be displayed on the image display to allow coarse alignment of the camera with the eye, and assist with coarse alignment using a focus estimation image processing algorithm that calculates a focus figure-of-merit and notifies the operator when the figure-of-merit exceeds a predetermined threshold, then activate the first light source and use the resulting captured image to automatically adjust the image exposure parameters and automatically adjust the variable power optical element to improve the image focus. The controller is then operated to activate the second light source and acquire one or more images of the fundus while the second light source is activated.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE SEVERAL VIEWS OF THE DRAWING

The foregoing and other objects, features and advantages of the invention will become apparent from the following description in conjunction with the accompanying drawings, in which reference characters refer to the same parts throughout the different views. The drawings are not necessarily to scale; emphasis has instead been placed upon illustrating the principles of the invention. Of the drawings.

DETAILED DESCRIPTION

Figure 1:
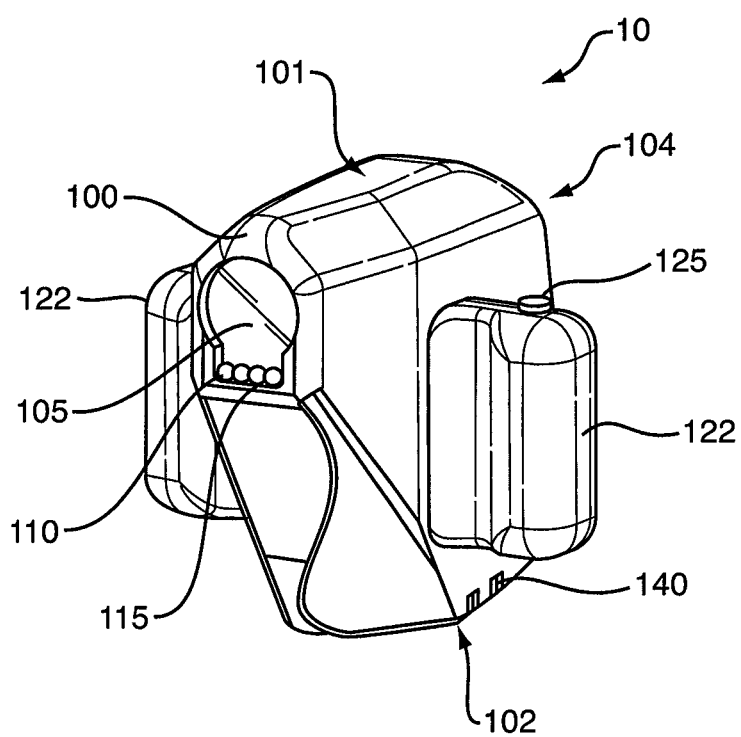
FIG. 1 is a representational drawing of an embodiment of the camera in its housing as seen by a patient.

As illustrated in FIG. 1, a portable retinal camera (PRC) 10 comprises a hand held housing 100 containing multiple light sources, image sensors, and optical elements. Housing 100, in some embodiments, also contains a digital microprocessor/controller programmed, for example, to accept user input, to direct the internal image acquisition processes, to present information to the user on a display, to label and store images, and to transmit images and ancillary data to an external communications channel. The housing also typically contains user interface elements, communications elements, structural elements, power supply elements, and other components that will be understood by one of skill in the art as needed to assemble and operate a portable electro-optical apparatus.

Figure 3:
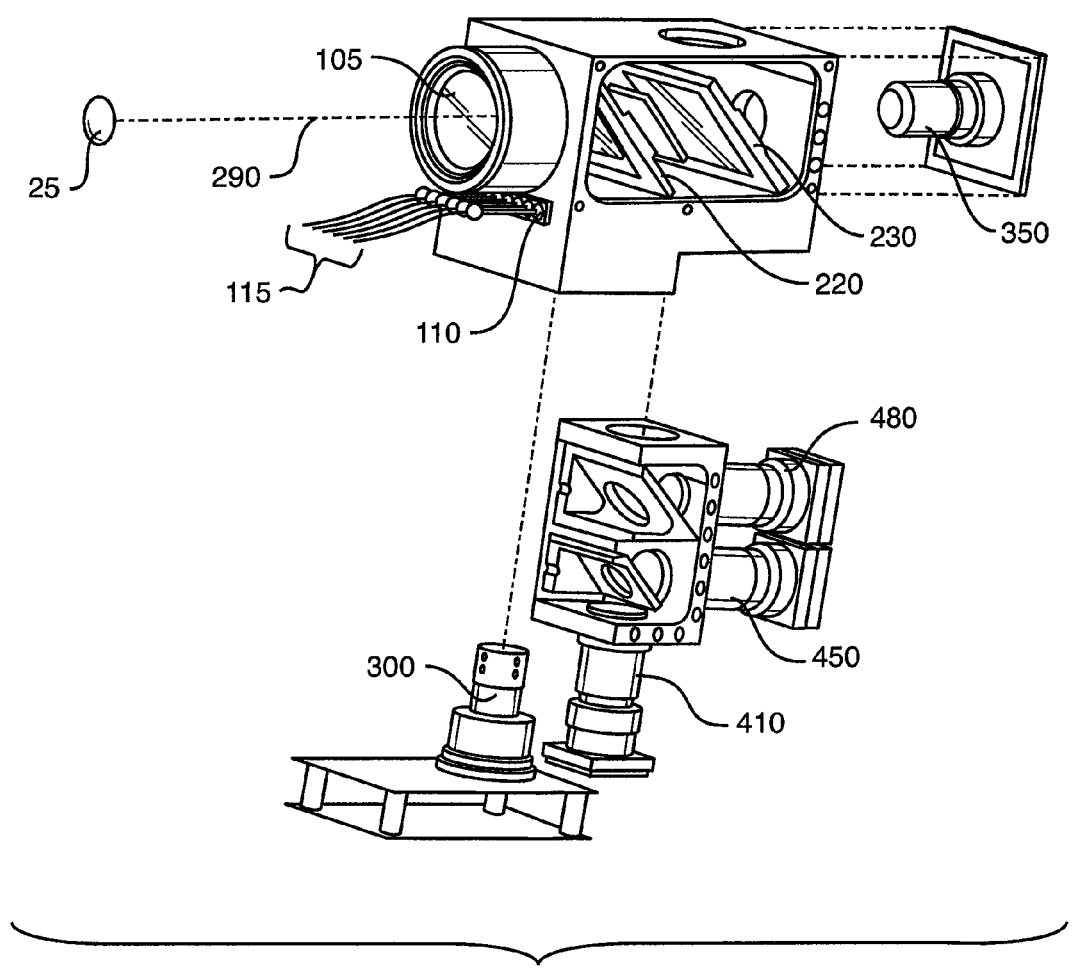
FIG. 3 is a partially exploded, isometric drawing of an embodiment of the electro-optical components of the camera as seen from the patient-facing side of the camera.

As further shown in FIG. 1 and FIG. 3, PRC 10 comprises an image acquisition aperture 105 and may comprise a anterior illuminator 110. Acquisition aperture 105 may be filled by the front element 205 of an imaging objective, whose operation is discussed below in conjunction with FIG. 5, or it may be filled with a protective window.

In some embodiments, anterior illuminator 110 provides a generally uniform illumination of the anterior of the eye and is preferably disposed below the optical system axis 290 between the center of acquisition aperture 105 and a patient's cornea 25, wherein for reference purposes PRC 10 comprises a top 101, a bottom 102, a front (patient-facing) 103, and a back (user-facing) 104. Therefore, "below the axis" is understood to mean at some location between axis 290 and bottom 102. In some embodiments, such as illustrated in FIG. 1, anterior illuminator 110 may be disposed behind a window.

In a preferred embodiment, anterior illuminator 110 comprises one or more anterior light emitting diodes (LEDs) 115, as shown in the partially exploded functional illustration in FIG. 3. Preferably anterior LEDs 115 emit in the deep red or near-infrared (NIR) region of the optical spectrum.

In some embodiments, housing 100 has attachment fixtures for one or more device-to-patient stabilization components, for example, a chin or forehead rest. These stabilization components are not illustrated.

Figure 2:
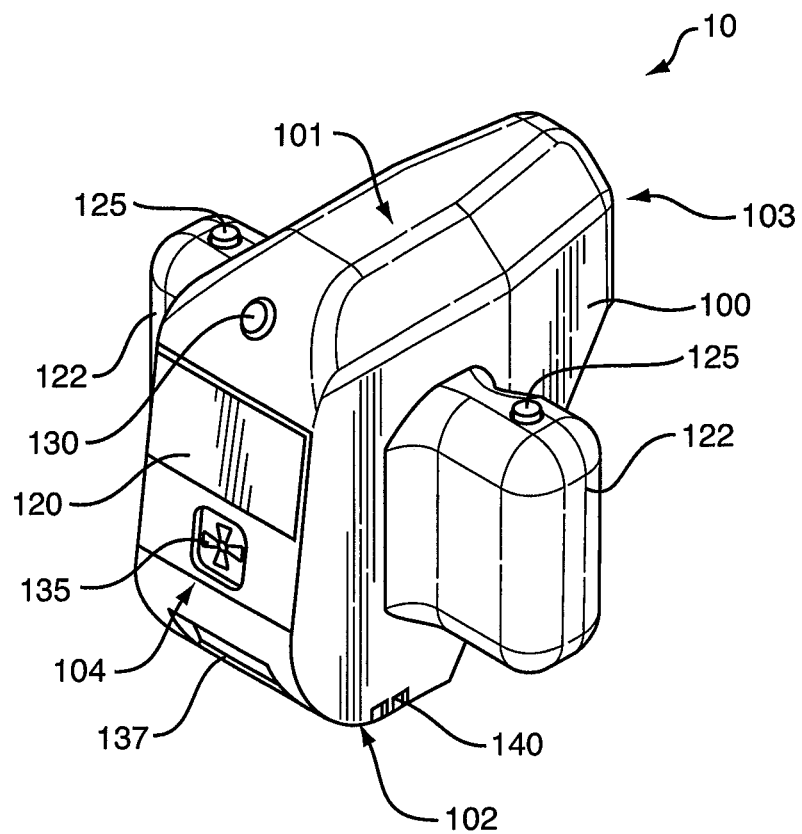
FIG. 2 is a representational drawing of an embodiment of the camera in its housing as seen by an user.
Figure 4:
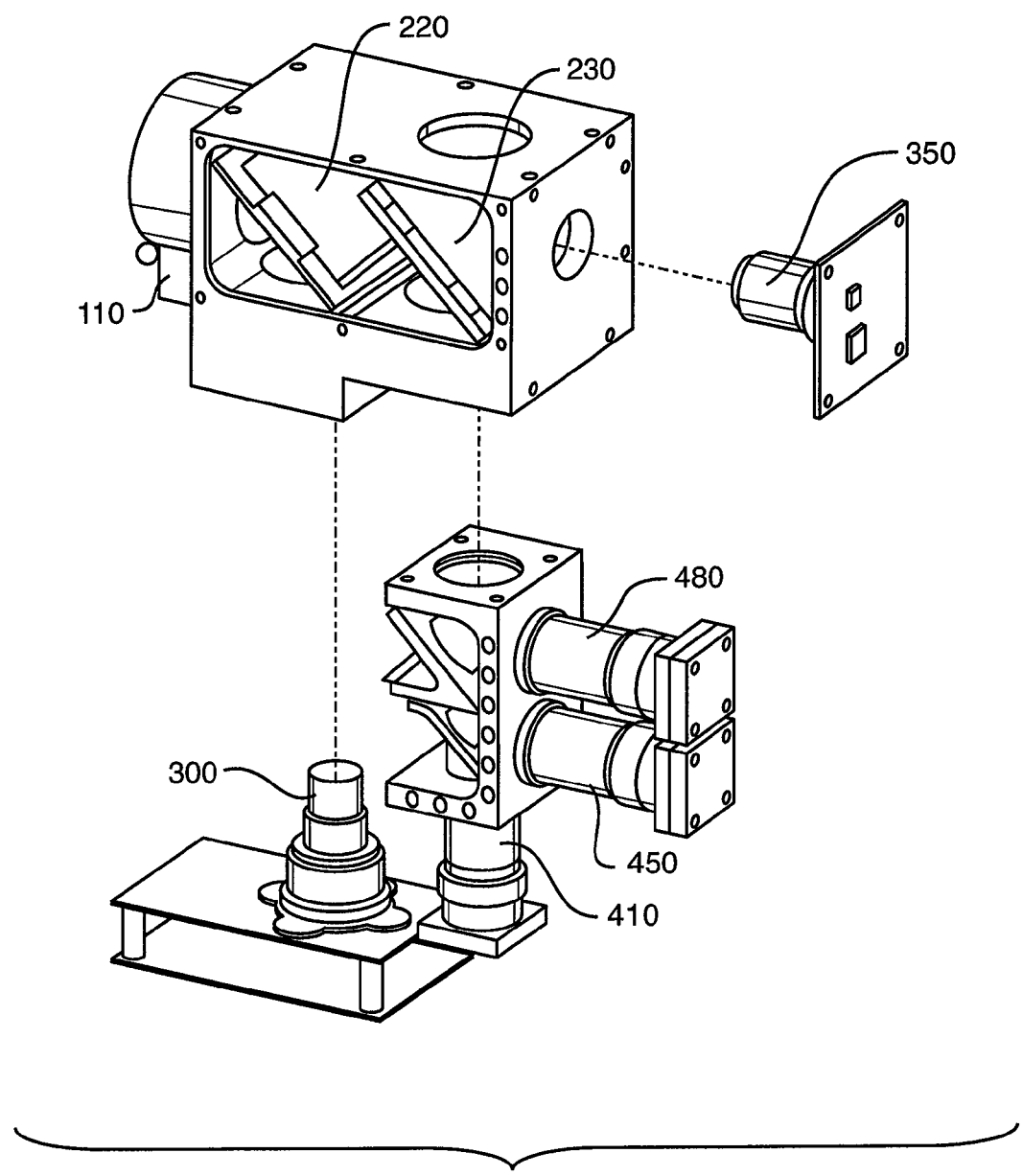
FIG. 4 is a partially exploded, isometric drawing of an embodiment of the electro-optical components of the camera as seen from the user-facing side of the camera.

FIGS. 2 and FIG. 4 illustrate the user's view of PRC 10. Housing 100 is generally bilaterally symmetric, permitting the user to image either eye of a patient without making any changes to the PRC configuration. In the illustrated exemplary configuration, a power switch 130 is located centrally on near the top of the rear 104 of PRC 10. A digital display screen 120 and a switch cluster 135 are also disposed on rear 104. In a preferred embodiment, PRC 10 is powered by rechargeable batteries placed below optical axis 290 to balance the center of gravity for best ergonomics and stability during alignment. An exemplary set of contacts 140 for connecting the batteries to a charging station are illustrated in FIG. 2. In a preferred embodiment, the contacts are eliminated and PRC 10 is inductively coupled to a charging station.

Symmetrical handles 122 are installed on the left and right sides of housing 100 and each handle 122 has a thumb-operable trigger 125 for initiating functions such as image capture. Symmetric handles are preferred over a single handled device, said symmetric configuration being equally convenient for left- or right-handed users. In addition, a two-handed grip is generally more stable than a one handed grip.

The bottom 102 of PRC 10 may include an industry standard "tripod" mounting threaded hole which is used for attaching a tripod, monopod, or tabletop stand if desired.

Figure 5:
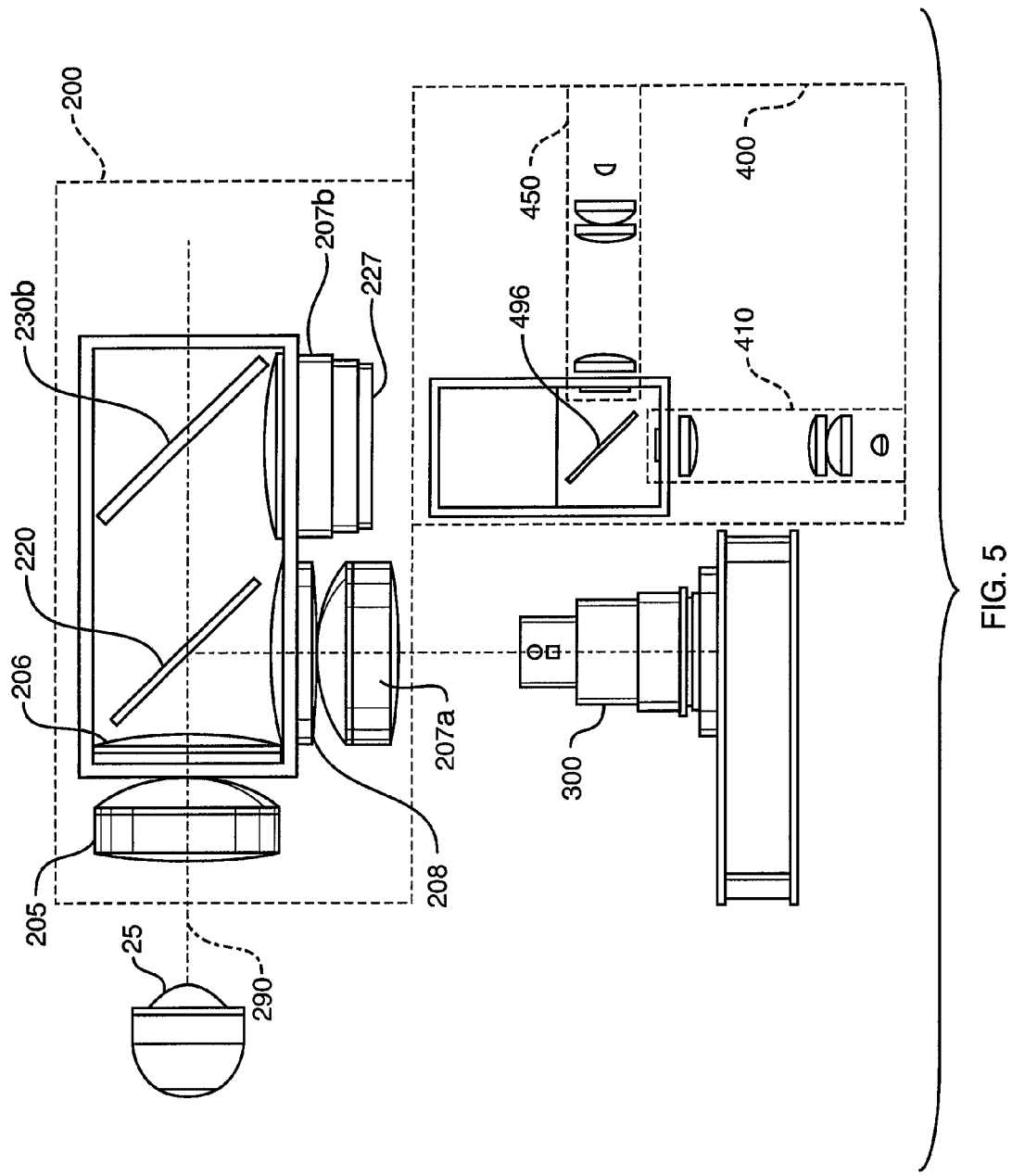
FIG. 5 is a side view, functional representation of the electro-optical elements in one embodiment of the camera.

PRC 10, in an embodiment illustrated functionally in FIG. 5, comprises two sources of illumination, an image sensor and a multiple branch optical system in which a number of beamsplitting elements are used to direct light between and among the sources, the eye, and the sensor. The sensor in this embodiment of PRC 10 is a Fundus Camera (FUNcam) 300, comprising a sensor chip and associated optical elements, and the sources of illumination are an AutoFocus Illuminator 450 (or AF Illuminator) and a (retinal) White Illuminator 410.

Figure 6:
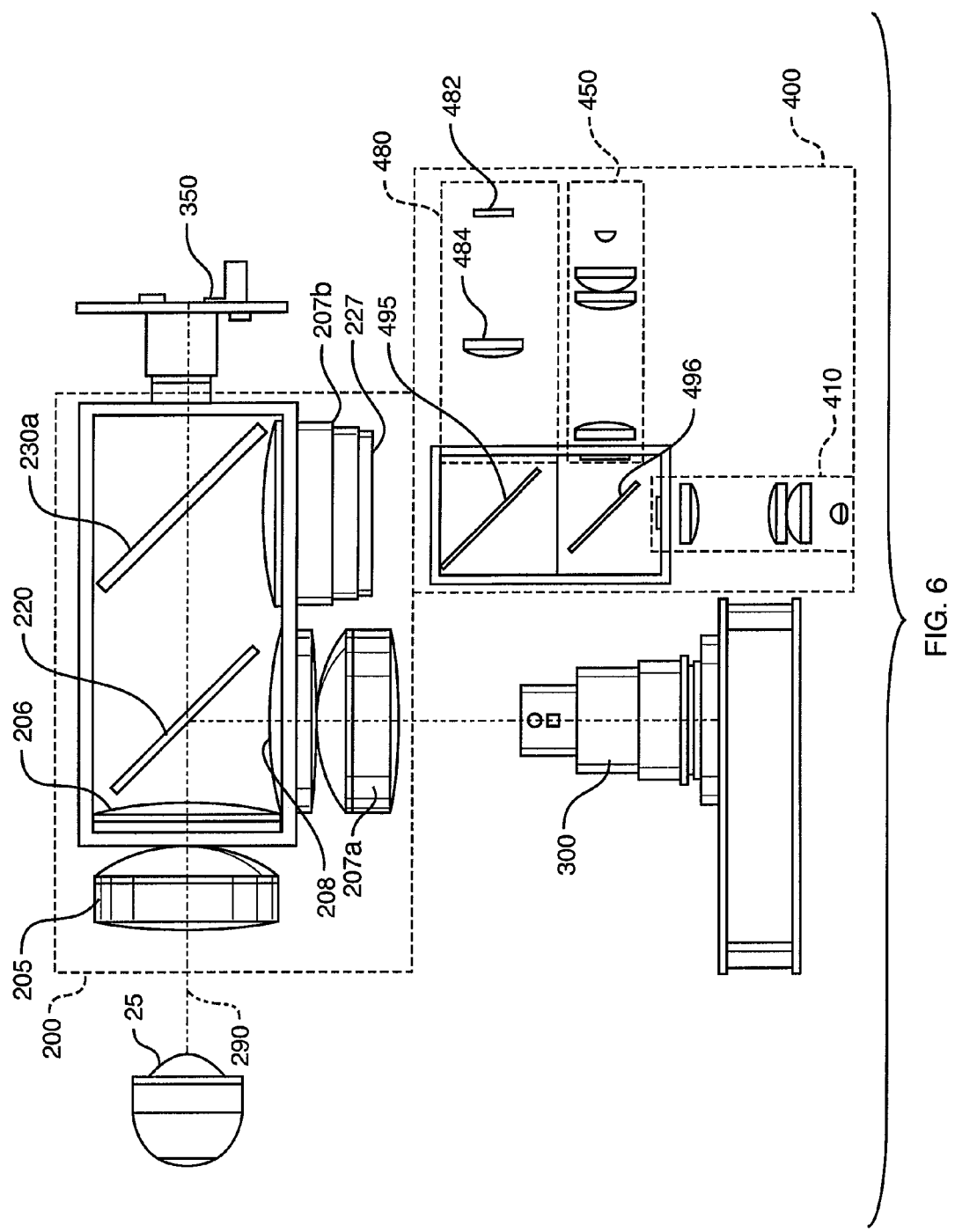
FIG. 6 is a side view, functional representation of the electro-optical elements in a second embodiment of the camera.

PRC 10, in a preferred embodiment illustrated functionally in FIG. 6, comprises three sources of illumination, two image sensors and a multiple branch optical system in which a number of beamsplitting elements are used to direct light between and among the sources and sensors. The two sensors in PRC 10 are an Anterior Camera (ANTcam) 350, comprising a sensor chip and associated optical elements, and the FUNcam 300 and the three sources of illumination are the Anterior Illuminator (not illustrated), the AF Illuminator 450, and the White Illuminator 410. In some embodiments ambient light is used instead of the Anterior Illuminator.

The preferred embodiment of PRC 10 illustrated in FIG. 6 further comprises a Fixation Target Illuminator 480. Fixation Target Illuminator 480, in general terms, is an optical projector that presents an image of a target to the patient, where the image is generally at or near infinity. In one preferred embodiment, Fixation Target Illuminator 480 comprises a number of user selectable point targets, for example LEDs, each target located at a different field angle relative to the optical axis 290 of PRC 10. When the patient looks at these off-axis targets, different areas of the retina may be imaged. In another embodiment the target in Fixation Target Illuminator 480 comprises an extended object (viz., a picture). In yet another embodiment the target comprises an electro-optic display device, e.g., a liquid crystal display, on which any suitable target image may be created, changed, or moved electronically. In a preferred embodiment the fixation system operates in the general wavelength region of peak visual response, i.e., green light.

The multiple branch optical system, although illustrated in FIG. 5 and FIG. 6 as four (sub) assemblies (an Objective Assembly 200, ANTcam 350, FUNcam 300, and an Illuminator Assembly 400), is best understood by describing each optical path therein individually, as is done below, recognizing that any particular optical element may used in more than one optical path. In a preferred embodiment the optical paths can be identified as: White Illuminator-to-Eye, AF Illuminator-to-Eye, Eye-to-FUNcam, and Eye-to-ANTcam. Additionally, in a preferred embodiment, there is a Fixation target-to-Eye path. Note that in preferred embodiments the anterior illuminator shines on the eye with no intervening optical elements. Less preferred embodiments may comprise only the White Illuminator-to-Eye, AF Illuminator-to-Eye, and Eye-to-FUNcam paths.

Figure 13:
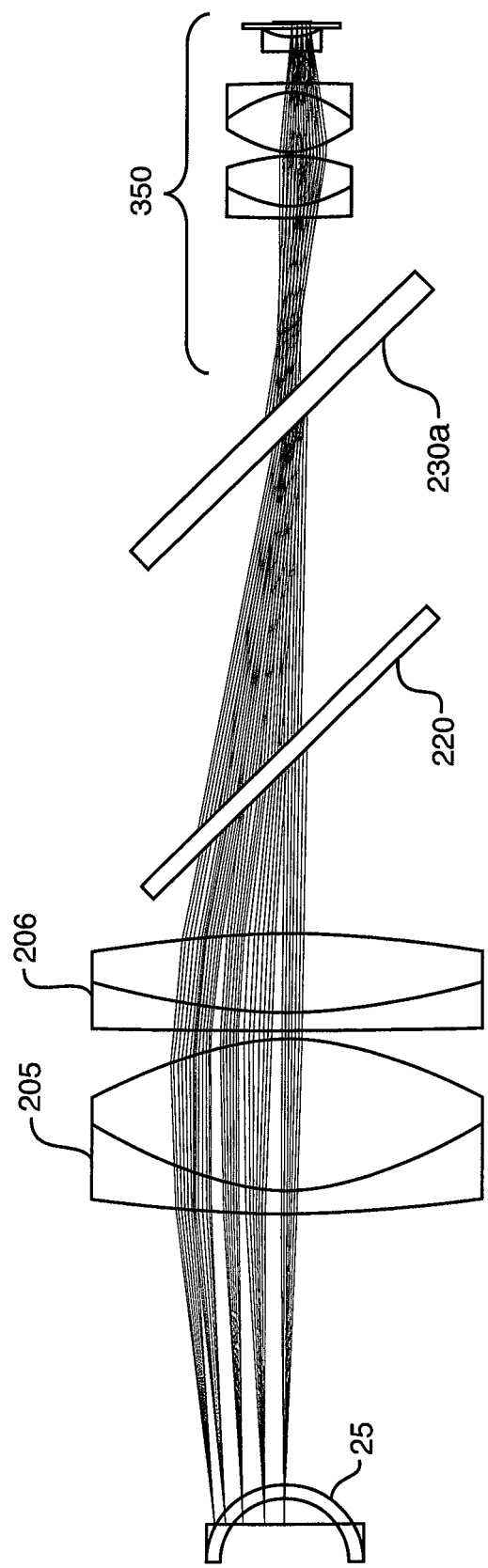
FIG. 13 is an optical layout drawing of the Anterior imager optical path.

The electro-optical elements in one preferred embodiment of PRC 10 are shown in FIG. 6. A typical image acquisition session begins when anterior of the eye 25 is illuminated by ambient light or by the anterior illuminator 110, not shown in FIG. 6. This light propagates to the ANTcam sensor chip 368 via the Eye-to-ANTcam optical path, described below and illustrated in FIGS. 13 and 14.

Eye-to-ANTcam optical path—A portion of the light leaving the anterior of the eye enters PRC 10 through acquisition aperture 105. Aperture 105 is also the entrance to an Objective Assembly 200. Inside Objective Assembly 200 the light passes sequentially through optical objective element 205 and optical objective element 206, a FUNcam Beamsplitter 220, and an Illumination Beamsplitter 230A. The light exits Assembly 200 and enters an ANTcam 350.

Optical objective element 205 and optical objective element 206 in combination with optical elements in ANTcam 350 form an imaging telescope that forms an image of the anterior of the patient's eye on ANTcam 368. In one preferred embodiment, the optics design corrects for the cornea portion of an eye model (specifically corrects for Field Curvature, Spherical, Chromatic (axial & lateral), Astigmatism, Coma). Using the objective elements that are common to all the branches of the multiple path optical system, preferred embodiment is optimized at f/5.0, which has depth of field of about ±1.5 mm. This preferred embodiment is insensitive to the tilt of FUNcam Beamsplitter 220 and Illumination Beamsplitter 230A plates, as these are in collimated space. Although the design allows for about 13% distortion, this level of distortion is acceptable, given the coarse alignment function performed by ANTcam 350.

Figure 14:
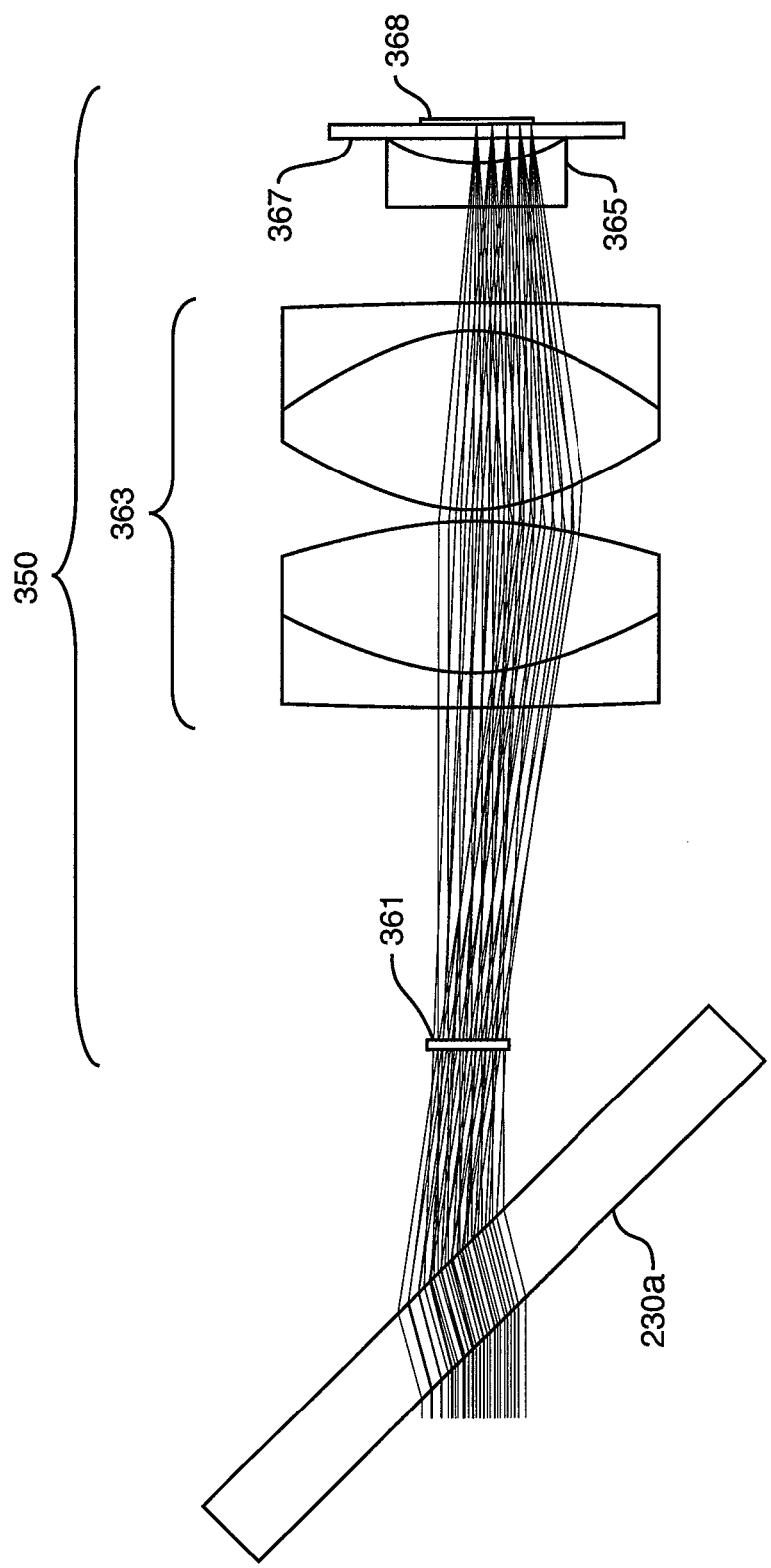
FIG. 14 is an enlarged portion of the optical layout drawing of FIG. 13.

ANTcam 350 is illustrated in more detail in FIG. 14. Light enters ANTcam 350 through an aperture stop 361. In one preferred embodiment the stop is 2.12 mm to set the f-number of ANTcam 350 to f/5.0. In other embodiments the stop size may be adjustable, either manually or electronically. After passing through aperture stop 361 the light is formed into an image on ANTcam 368, through ANTcam window 367, by imaging lens pair 363. Typically, ANTcam sensor 368 is a monochrome (viz., "black and white") digital imaging array having a moderate (VGA) pixel density to support coarse alignment. In one preferred embodiment the ANTcam sensor is a ⅓-Inch Wide-VGA Digital Image Sensor such as model MT9V024, available from Aptina Imaging Corporation (3080 North 1st St. San Jose, Calif. 95134, USA).

It will be understood by one of skill in the optical design art that there is no single preferred design for the optical element parameters used in the PRC. These design choices depend heavily on the design criteria used and the external conditions imposed (e.g., cost, weight, size, etc.). The exemplary designs presented herein are in no way intended to be limiting to the scope of the claimed invention.

Figure 7:
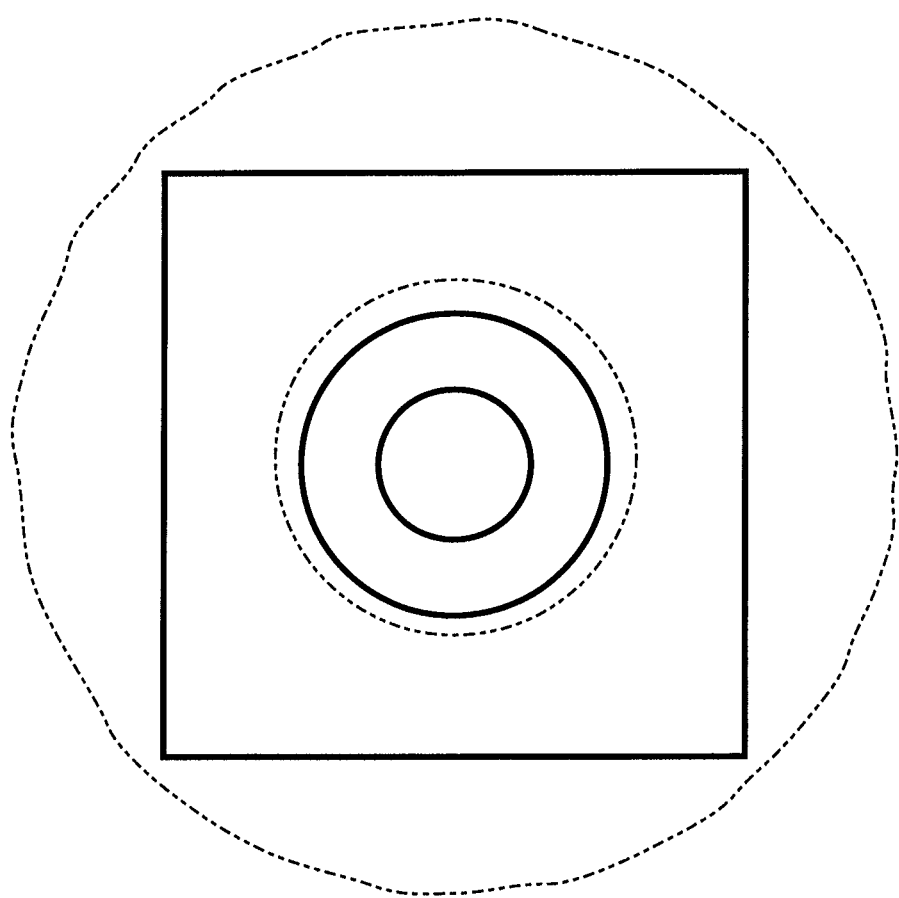
FIG. 7 illustrates the coarse alignment fiducial overlaid on a iris image.

The image of the anterior region of the eye (viz., the iris and pupil) detected by the ANTcam is presented on display screen 120 to provide feedback to the user as he moves PRC 10 to manually achieve coarse alignment (viz., vertical and lateral positioning [X and Y axes]) and coarse focus (viz., axial positioning [Z axis]). Lateral alignment is determined by centering the image of the pupil on circular fiducial marks overlaid on the image, as illustrated in FIG. 7. Once the user has manually located PRC 10 so that the pupil appears within the fiducial, as shown in the figure, the PRC's AutoAlignment function recognizes the pupil image and initiates its focus estimation image processing algorithm. This algorithm continually calculates a focus figure-of-merit as the user attempts to focus PRC 10 by watching the image on display screen 120 while moving PRC 10 towards and away from the patient. When the figure-of-merit exceeds a pre-determined threshold the user is notified that adequate focus has been achieved by a feedback mechanism. Such feedback may be graphical (e.g., symbols, fiducial color change, flashing fiducials on a display), visible (e.g., an indicator light), tactile (e.g. a vibration), audible (e.g., a beep), or a combination of these. The notification is preferably graphical or visible so that it can remain illuminated continuously without disturbing the patient or annoying the user.

Once the autoalignment system is satisfied that the coarse lateral and axial alignments have been achieved, it may automatically initiate the next phase of image acquisition by turning on the AF Illumination and the FUNcam, thus bringing the AF Illuminator-to-Eye and Eye-to-FUNcam paths into play. Alternatively, the system can be operated in manual acquisition mode wherein this next phase is initiated by the user, typically by pressing one of PRC 10's finger-operable triggers 125.

Figure 9:
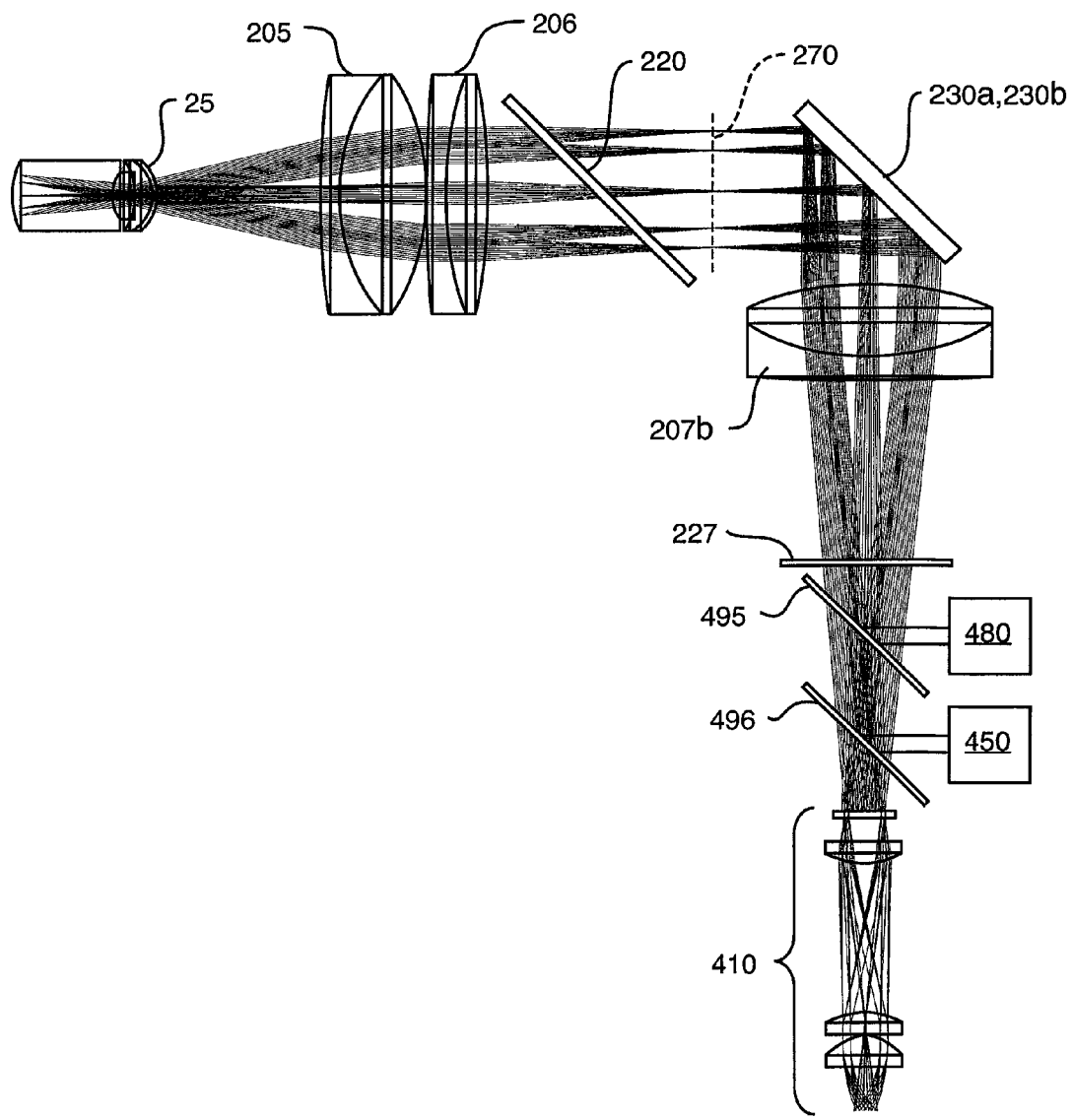
FIG. 9 is an optical layout drawing of one embodiment of the illumination optical path.
Figure 10:
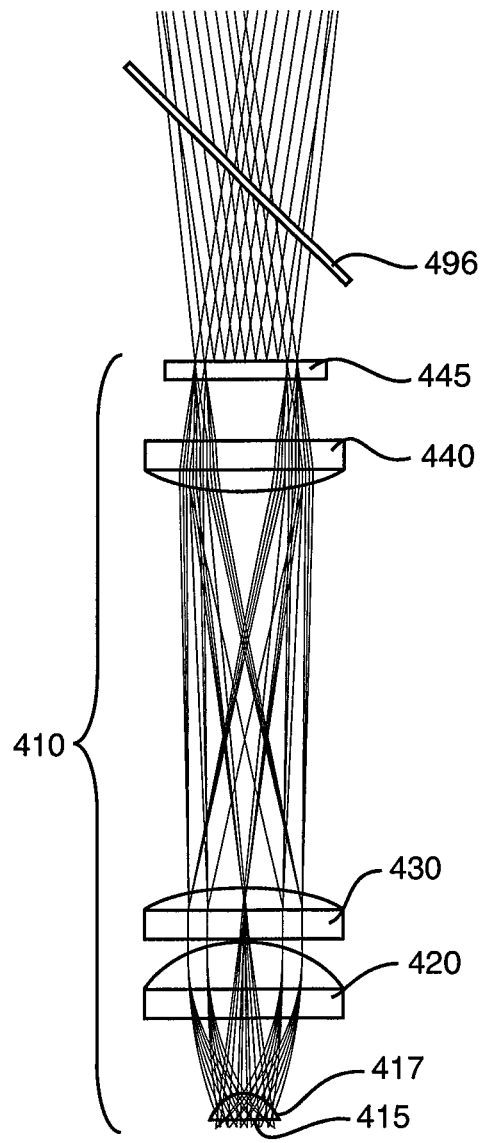
FIG. 10 is an enlarged portion of the optical layout drawing of FIG. 9.

AF Illuminator-to-Eye optical path and White Illuminator-to-Eye optical path—The optical path from the AF Illuminator to the eye and the optical path from the White Illuminator to the eye are substantially identical, with the two illuminator modules being brought together to illuminate the eye from opposite sides of a beam combining optic. Thus, without loss of generality, an embodiment of the White Illuminator is described herein and one of skill in the art will readily understand that the AF Illuminator is only different in regards to the specific source (monochromatic, NIR compared to broadband, white) and the optical element design parameter changes to accommodate the different source, such as changes in optical materials and coatings. FIG. 9 is an optical layout diagram of the complete White Illuminator-to-Eye optical path and FIG. 10 is a detail drawing of the White Illumination module.

As will become apparent later, a feature of a preferred embodiment of the multiple branch optical system is the use of the Gullstrand principle of illumination, which is also the method used by many ophthalmic instruments. The purpose of this type of illumination is to provide an image that is relatively free of reflected light from the cornea and other common path optics. The principle involves separating the illumination and imaging paths in the patient's pupil plane.

Figure 8:
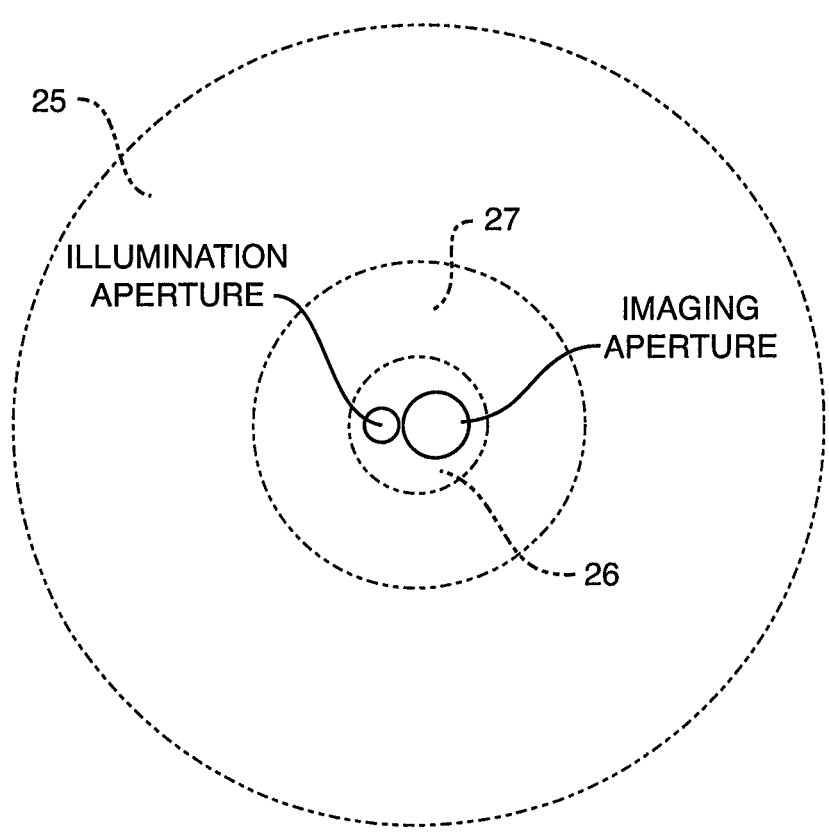
FIG. 8 illustrates the Gullstrand principle of illumination system design.

The light from an illumination source is passed through an aperture stop in PRC 10, which stop is then imaged onto the patient's pupil. Passing through the patient's pupil, the light illuminates the retina. Traveling in the reverse direction, the light carrying the image information from the retina to PRC 10 must also pass through the patient's pupil. Inside PRC 10 this image light follows a separate path to reach the imaging (FUNcam) sensor chip 342. In accordance with the Gullstrand approach, the separate aperture stop in this branch of the optical system is conjugate to a different part of the pupil plane. This approach minimizes the reflections from the cornea that reach the image sensor chip. FIG. 8 is an illustration of an eyeball overlaid with depictions of the optical system's illumination and imaging aperture stops. As observed from this head-on view, a pupil 26 is the circular aperture in the center of an iris 27.

In a preferred embodiment PRC 10 is designed to operate without dilating the patient's pupil, which requires that the images of the two apertures be small and closely space. In one preferred embodiment, FUNcam 300 will image through a 2 mm diameter aperture at the pupil plane and the illumination will pass through a 1 mm diameter aperture.

Returning to FIG. 9 and FIG. 10, each illuminator-to-eye optical path comprises a light source, typically and preferably one or more LEDs, but possibly mini-halogen lamps, or flashlamp(s). FIG. 10 illustrates the White Illuminator source assembly 410. The LED source 415 may comprise a single LED die or may comprise multiple dies. In one preferred embodiment, White LED source 415 comprises a 4 die assembly such as the LE UW S2W available from Osram Opto Semiconductors, GmbH (Leibnizstrasse 4, D-93055 Regensburg, Germany). The LE UW S2W has a color temperature of approximately 6000 K and a total radiating surface of 2×2 mm^2. In the preferred embodiment each of the 4 dies can be activated individually. Light leaving the surface of the die(s) passes through a small hemispherical beam shaping lens 417 and a pair of lenses 420,430 that form a Kohler condenser configuration. The light passes through a second beam shaping lens 440 before creating an image of the LED die in the plane of an illumination aperture stop 445. Aperture stop 445, in keeping with the Gullstrand principle, is imaged onto the patient's pupil. In one preferred embodiment aperture stop 445 is an annulus. Whereas the four die LED source 415 is imaged onto aperture stop 445, it is possible in this embodiment to illuminate one, two, three, or four 90 degree annular arcs.

As was mentioned above, the AF Illuminator source assembly 450 is in all substantive aspects identical to White Illuminator source assembly 410, once the wavelength difference is taken into consideration. For example, lenses 420, 430, and 440 in assembly 410 have the same diameters and focal lengths as their corresponding lenses in assembly 450; only the anti-reflection coatings are different. The major difference between the two illuminators is, not surprisingly, the source LED. A deep red LED emitter is preferably used in AF Illuminator source assembly 450. In one embodiment this LED is a model LZ1-00R205, available from LedEngin, Inc. (3350 Scott Blvd. Bldg. #9, Santa Clara Calif. 95054, USA), which is a single die source emitting at approximately 660 nanometers, packaged with an integrated glass dome element, which corresponds to hemispherical lens 417 in the White Illuminator source assembly 410.

As shown in FIG. 9, source modules 410 and 450 each project beams toward beam combiner 496, albeit from opposite sides of the combiner. Combiner 496, in one preferred embodiment, is an uncoated, "ultrathin" (0.2 millimeter) glass plate wherein Fresnel reflection directs about 8% (total, both surfaces) of the AF Illuminator light toward the eye whilst about 90% of the White Illuminator light is transmitted toward the eye. The remainders of these two branches of the multiple path optical system are literally identical.

In some embodiments the combined beam propagates directly to illumination objective 207B. In other, more preferred, embodiments the combined beam propagates through a linear polarizer 227 before reaching objective 207B. As will be described below, linear polarizer 227 may be beneficially used in combination with a polarizing beamsplitter to suppress specular reflections of the illumination light from the cornea and other optical elements from reaching the image sensor, FUNcam sensor chip 342. In some preferred embodiments, namely those embodiments incorporating Fixation Target Illuminator 480, the combined beam traverses a Fixation Target beam combiner 495, which is another uncoated, "ultrathin" (0.2 millimeter) glass plate. As will be described below, Fixation Target Illuminator 480 is preferably operated at or near the peak wavelength of visual sensitivity, viz., green light.

Linear polarizer 227 is oriented such that the transmitted light is polarized perpendicular to the plane of the drawing in FIG. 9. Other embodiments operate where the light is polarized parallel to the plane of the drawing. Additionally polarizer 227 must operate over the full spectrum of White LED 415 and deep red of the AF LED. In one preferred embodiment linear polarizer 227 is a wire grid polarizer such as model PPL-05c available from Moxtek, Inc. (452 West 1260 North, Orem, Utah 84057, USA).

The combined beam enters Objective Assembly 200 and passes through, sequentially, optical objective element 207B, optical objective element 206 and optical objective element 205, which objective elements together have been designed to form an image of aperture stop 445 in the plane of the patient's pupil, thereby implementing an illumination system compatible with the Gullstrand principle. The illuminator light passing through the patient's pupil must do so with an adequately large cone to illuminate a usefully large region of the retina. The specific design requirements are subject to PRC 10's designer's goals. However, in one preferred embodiment the cone angle is 45 degrees.

The illuminator optical path(s) in PRC 10 include a FUNcam beamsplitter 220. This beamsplitter is used to send the light returning from the retina to the FUNcam. In a preferred embodiment, FUNcam beamsplitter 220 is a polarizing beamsplitter, wherein polarized, specular reflections of the illuminator light from the cornea and optical objective elements 205, 206 are allowed to pass backward through the beamsplitter whilst the orthogonally polarized component of the diffusely reflected light from the retina are sent to the FUNcam. From the optical design perspective of the illuminator paths, FUNcam beamsplitter 220 is just a tilted window in quasi-collimated space.

In some embodiments, Objective Assembly 200 additionally comprises a fold mirror 230B, which mirror is provided for convenience to create a more compact optical layout for PRC 10. In some preferred embodiments, fold mirror 230B is replaced with Illumination Beamsplitter 230A. Beamsplitter 230A is used in systems in which coarse alignment is preformed using an ANTcam subsystem. In one preferred embodiment Illumination Beamsplitter 230A is a 70/30 R/T beamsplitter designed for broad spectrum applications such as model NT49-756 available from Edmund Optics Inc. (101 East Gloucester Pike, Barrington, N.J. 08007-1380, USA). Furthermore any of these beamsplitters may be rotated about their optical axis to change the packaging layout for a more compact housing provided the configuration's polarization of operation is not compromised.

As has been discussed above, optical objective elements 205, 206 are also part of the Eye-to ANTcam optical path, if ANTcam 350 is present in the embodiment. As will be discussed below, these same two optical objective elements are part of the Eye-to-FUNcam optical path. Thus it is generally important to design all segments of the multiple branch optical system as the overlapping, integrated system it is. As is well known in the art, there is no one optical design solution that will be best for every use; each designer will develop optical system specifications based on specific design goals and constraints.

Figure 11:
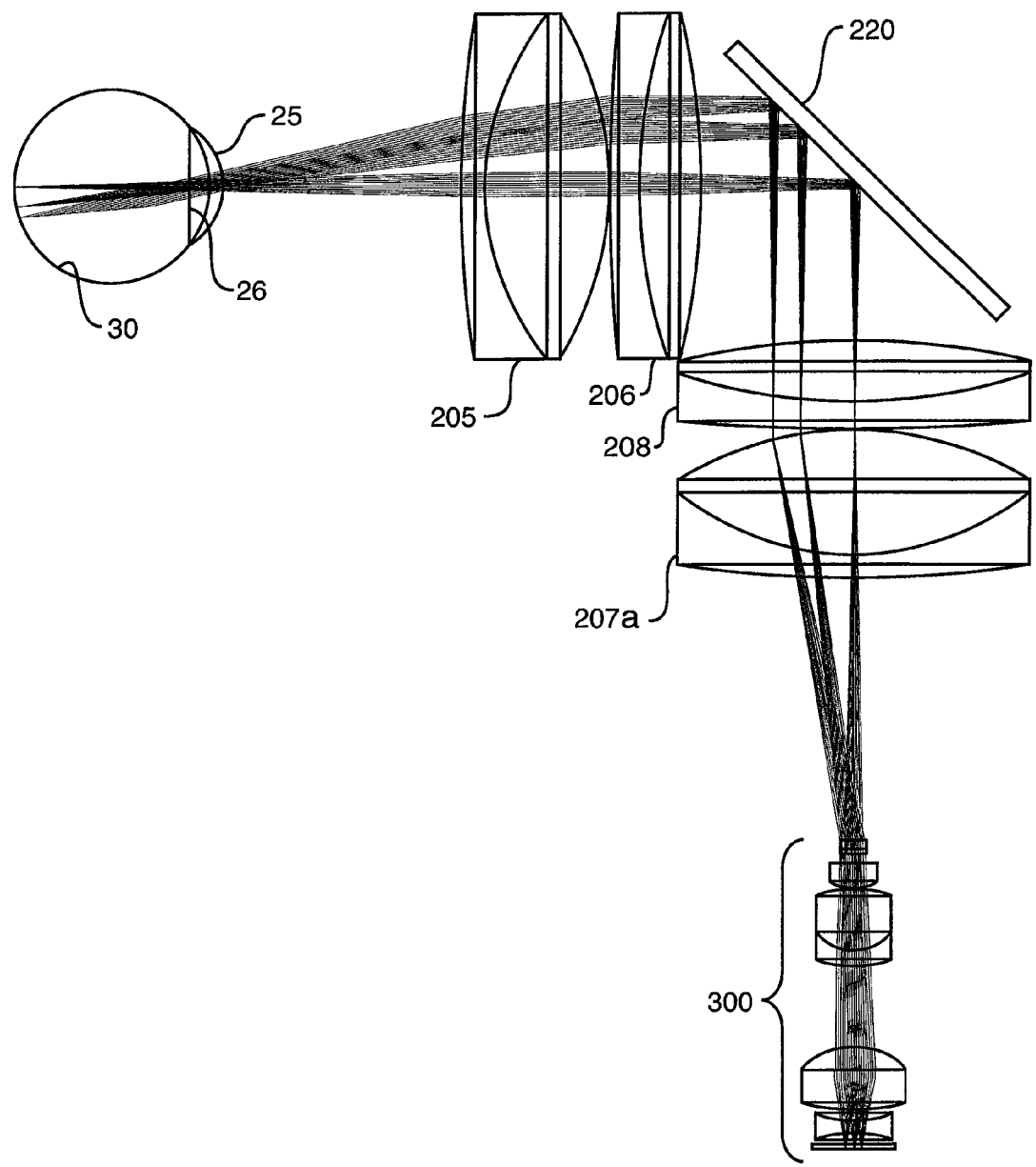
FIG. 11 is an optical layout drawing of the Fundus imager optical path.
Figure 12:
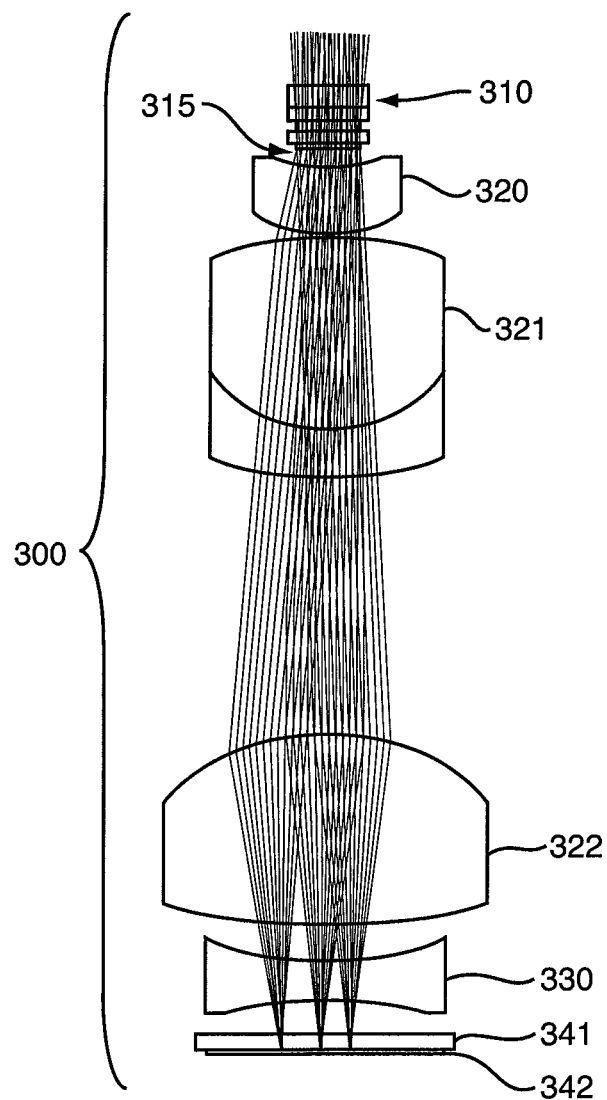
FIG. 12 is an enlarged portion of the optical layout drawing of FIG. 11.

Eye-to-FUNcam optical path—The last substantive optical path in the multiple path optical system is the Eye-to-FUNcam optical path. This optical path, illustrated in FIG. 11 and FIG. 12, is the primary path in PRC 10 insofar as it is the path by which the clinically valuable retinal images are obtained. As shown in FIG. 11, the optical design is divisible into a front end (housed in Objective Assembly 200) and a FUNcam 300. The front end Objective Assembly 200 comprises, in a preferred embodiment, a split symmetric objective lens. The front half of this objective lens is formed by optical elements 205, 206 and the back half by optical elements 208, 207A, wherein the later elements are symmetrically flipped copies of the former elements. That is, the front half and the back half of this form of objective lens are mirrored versions of each other. The two halves of the split objective are separated by FUNcam beamsplitter 220 which acts as a fold mirror to direct the light from the retina toward FUNcam 300.

By design, and in keeping with the Gullstrand principle, this objective lens has an external pupil. The pupil is located at the patient's pupil 26 when PRC 10 is correctly positioned axially with respect to the patient. Pupil 26 is preferably imaged onto a FUNcam aperture stop 315 in FUNcam 300. FUNcam aperture stop 315 is preferably designed so that its image in pupil 26 is non-overlapping with the image of illuminator aperture stop 445 in pupil 26. In a preferred embodiment the image of FUNcam aperture stop 315 is a 2 millimeter disk in the patient's pupil 26.

Furthermore, in a preferred embodiment, the front half of the objective lens, viz., optical elements 205, 206, when operating through a typical human eyeball, forms an intermediary image of a retina 30 in the space between the two halves of the split objective. Preferably, this intermediary image is formed away from any physical surface on which dirt and/or scratches might be found.

Light from retina 30 exits Objective Assembly 200 and enters FUNcam 300, illustrated in FIG. 12. As mentioned above, Objective Assembly 200 forms an image of the patient's pupil on an aperture stop 315 in FUNcam 300. This stop is also the optical stop for the relay assembly, formed by a variable power optical element 310 and lens 320, lens 321, lens 322, and field flattening lens 330. Preferably the effects of a window 341 are considered in the design of FUNcam 300. In one preferred embodiment FUNcam 300 can resolve features in object space (i.e., on the retina) of 10 microns or less.

FUNcam 300 is the primary image capture device in PRC 10. Typically it is a digital array camera, which is readily available in many formats and using different technologies. Based on an understanding of clinical needs, the inventors have determined that a full-color, high resolution sensor is preferred. In one preferred embodiment the FUNcam sensor chip 342 is a 1/2.5-inch CMOS active-pixel digital image sensor with an active imaging pixel array of 2592H×1944V such as Micron® Imaging MT9P031, available from Micron Technology, Inc. (8000 S. Federal Way, P.O. Box 6, Boise, Id. 83707-0006, USA). The MT9P031's low-noise CMOS imaging technology achieves CCD image quality (based on signal-to-noise ratio and low-light sensitivity) while maintaining the inherent size, cost, and integration advantages of CMOS. It incorporates sophisticated camera functions on-chip such as windowing, column and row skip mode, and snapshot mode. It is programmable through a simple two-wire serial interface, making it well suited to PRC 10's varying needs.

It may be noted in FIG. 11 that Objective Assembly 200 includes FUNcam Beamsplitter 220. As has been described above, Beamsplitter 220 separates the illumination path(s) from the FUNcam imaging path. In a preferred embodiment Beamsplitter 220 is a polarizing beamsplitter that improves the isolation of FUNcam 300 from specular reflections. In one preferred embodiment FUNcam Beamsplitter 220 is a wire-grid polarizer, for example, model PBF02C, available from Moxtek, Inc. (452 West 1260 North, Orem, Utah 84057, USA).

Variable power optical element 310, disposed near the aperture (e.g. pupil) plane in FUNcam 300, provides PRC 10 with a fine focus capability. Unlike many office-based optometric or ophthalmologic instruments in which the patient and instrument are "locked" into position by head and chin rests, PRC 10 is preferably a hand-held, no-patient-contact device. The user is responsible for manually locating the camera coarsely at the correct distance from the patient but, generally, the instrument will have to provide automatic fine focus tracking to consistently achieve clinically acceptable retinal images. As will be described below, PRC 10 preferably comprises a closed loop automatic fine focus control driven by focus quality estimation signals derived from the real-time FUNcam image stream while the AF Illuminator is operating.

The control signals from the autofocus control module are sent to variable power optical element 310. This variable power optical element is preferably disposed substantially coincident with the pupil of the FUNcam, as shown in FIG. 12. At this location, as is well understood in the optical design arts, changes in optical power have the greatest effect on system focus. In some embodiments variable power optical element 310 is a optical element in which effective power changes are mechanically enabled. For example, a plano-concave optical element with its concave surface in contact with the convex surface of a matching plano-convex element will have no optical power, to first order. If these two elements are separated, their effective optical power increases in proportion to their separation. This separation can be controlled with an electrically driven displacement device.

Figure 15:
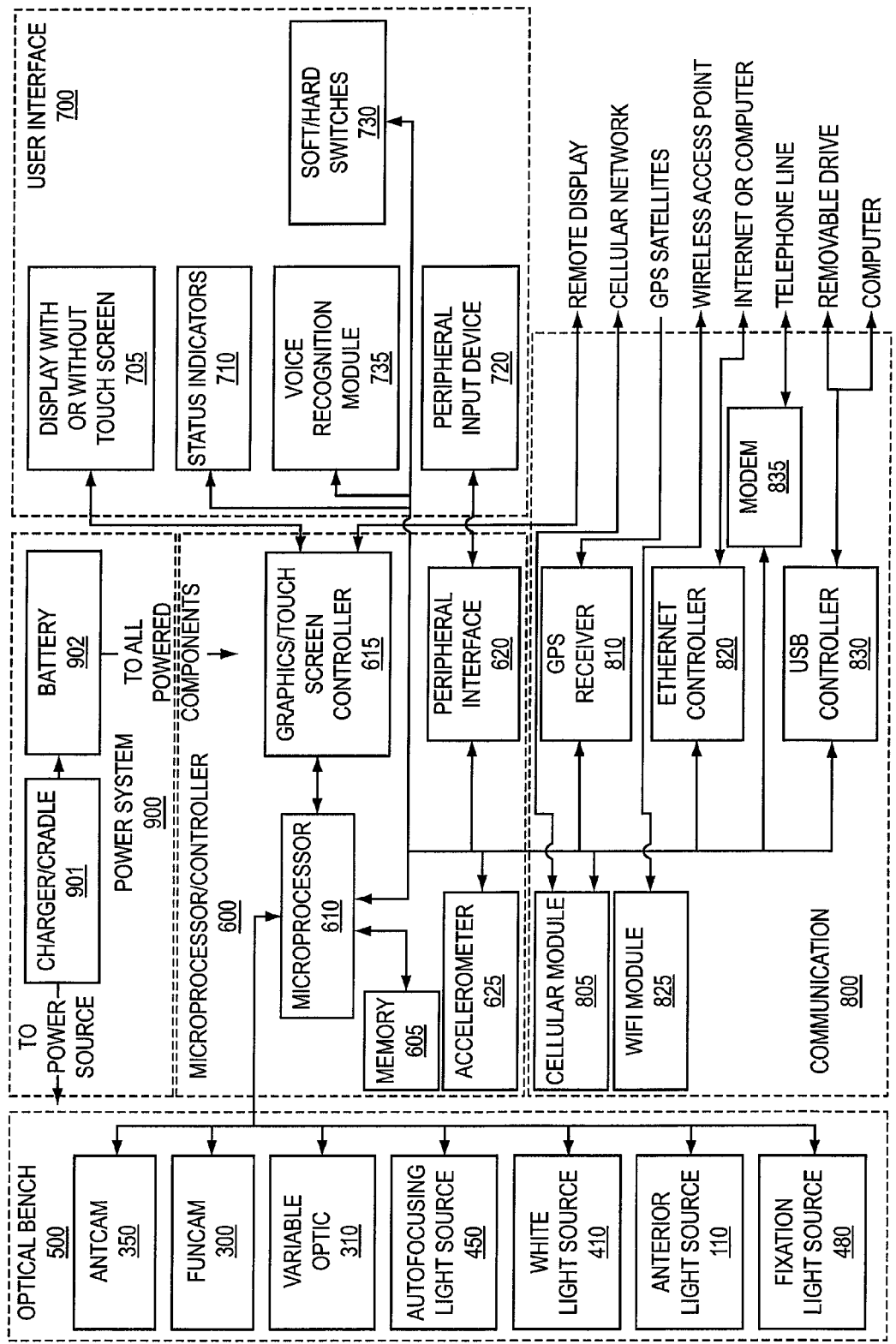
FIG. 15 is an electronics block diagram of an embodiment of the camera.

However, in a preferred embodiment, variable power optical element 310 is a "liquid" lens, such as the Varioptic, SA (Bâtiment Tony Garnier, 24B rue Jean Baldassini, 69007 Lyon-France, http://www.varioptic.com) model ARCTIC 416™ variable focus liquid lens. The design and operation of this lens is described in REF, which is included herein by reference. The liquid lens is based on the electrowetting phenomenon described herein: a water drop is deposited on a substrate made of metal, covered by a thin insulating layer. The voltage applied to the substrate modifies the contact angle of the liquid drop. The liquid lens uses two isodensity liquids, one is an insulator while the other is a conductor. The variation of voltage leads to a change of curvature of the liquid-liquid interface, which in turn leads to a change of the focal length of the lens. In another preferred embodiment, Varioptic SA liquid lens model A316S is used for variable power optical element 310. This lens offers optical image stabilization (OIS) technology. OIS is accomplished by the incorporation of multiple electrodes on the substrate. When differential voltages are applied between opposing electrodes, the optical beam is "steered", or deviated, to offset image shifting caused by inadvertent movements of the camera. Lens A316S is incorporated in a closed-loop configuration with the image processing system 600 (FIG. 15). When PRC 10 moves relative to the eye (due to shaking of the user's hand, or patient eye saccades, for example), the entire image shifts on image sensor 342 by a certain number of pixels in a certain direction ("shift vector"). The image processing system 600 calculates this shift vector on a frame-to-frame basis by computing factors relating to the patient's pupil in the ANTcam 350 video stream, such as the centroid of pupil edge segments. A look-up table (LUT) is then used to determine the correct voltage to be applied to specific electrodes on liquid lens model A316S to compensate for the shift vector. This differential voltage, applied to the electrodes, very rapidly corrects the deviation, i.e., returns the image to it's prior location on the image sensor. The closed loop control system must operate at a sample (frame) rate that is at least double the highest frequency movement to be corrected (Nyquist theorem). ANTcam 350 incorporates a CMOS image sensor 368 that is capable of very high frame rates when regions of interest (ROIs) are used. At full resolution (752×480 pixels) ANTcam 350 has a maximum frame rate of 60 fps. When imaging smaller ROIs, ANTcam 350 supports frame rates of over 200 fps. This is an adequate sampling rate to correct for most tremors and saccades. A programmable frequency roll-off is adjusted to ensure that high frequency movements are corrected but slower movements (e.g., intentional panning) are not.

Fixation Target Optical Path—Some embodiments of PRC 10 comprise a fixation target 482 towards which the patient is instructed to direct his gaze. See, for example, the embodiment illustrated in FIG. 6. The presence of a fixation target makes it much easier for the patient to maintain his eye a steady position. Additionally, having a target to view also helps the patient maintain a constant focus, say, at infinity.

In one embodiment fixation target 482 is a point-like source of light, e.g., an LED or small incandescent lamp. Preferably target 482 is green, at or near the peak of visual sensitivity. In a preferred embodiment target 482 is a part number 598-8081 LED available from Dialight Corporation, 1501 Route 34 South, Farmingdale, N.J. 07727, USA. The source is disposed in fixation target illuminator 480, which, in general terms, is an optical projector that presents an image of target 482 to the patient, where the image is generally at or near infinity. The design of the fixation target optical path inherently incorporates optical elements that are shared with other paths in the multiple branch optical system.

In this embodiment, and as illustrated in FIG. 6, fixation target illuminator 480 comprises the aforementioned point-like target 482, a single imaging lens 484, and a beam combiner 495. Imaging lens 484 forms a real image of target 482 inside objective assembly 200. It is known from the design of the previously described optical paths that a retinal image plane 270, shown in FIG. 9, exists in the air space between beamsplitter 220 and beamsplitter/fold mirror 230A/230B. Fixation target illuminator 480 projects its image of target 482 into that plane, thus ensuring that optical objective element 205 and optical objective element 206 project the target image to infinity. The light travels through the patient's cornea and eye lens and is focused on or near the retina, depending on the patient's ability to focus on infinity. Beam combiner 495 folds the fixation target illuminator optical path into substantially co-axial alignment with the optical paths for the AF and white illuminators. In a preferred embodiment, beam combiner 495 is an "ultra" thin, uncoated, plane parallel glass plate, such as catalog number NT66-189 from Edmund Optics Inc., 101 East Gloucester Pike, Barrington, N.J. 08007-1380, USA.

In another embodiment, imaging lens 484 is mounted on an axial motion (viz., focusing) stage. By moving the stage slightly, the patient will perceive the virtual image of the target at a different apparent distance. This focusing ability allows PRC 10 to compensate for individual patient refractive error (that is, compensate for a patient's need for glasses). The stage may be manually driven, e.g., by a hand activated screw thread, or the stage may be motorized, e.g., by a miniature rotary motor or a linear motor. A motorized stage may be controlled by the user or, preferably, by microprocessor/controller 600.

In a preferred embodiment, fixation target illuminator 480 comprises a number of user selectable point-like targets, for example LEDs, each target located at a different field angle relative to the optical axis 290 of PRC 10. In this embodiment the general configuration and function of Target Illuminator 480 is substantially identical to the single point-like target embodiment with the single target replaced with an array of targets. In one embodiment the target array comprises five sources arranged with one center ("on axis") source and one each on a circular locus at 0, 90, 180, and 270 degrees around the on axis source. This 4-cardinal point configuration could also be an eight or more cardinal point arrangement for investigating a particular patient's problem region. These multiple fixation targets allow the user to image different regions of the retina.

In another embodiment the target in fixation target illuminator 480 comprises an extended, back-illuminated object (viz., a picture). In yet another embodiment the target comprises an electro-optic display device, e.g., a liquid crystal display, on which any suitable target image may be created, changed, or moved electronically. In a preferred embodiment the fixation system operates in the general wavelength region of peak visual response, i.e., green light.

Electronics—PRC 10 is a semi-automated digital electronic camera. As such, digital electronics perform multiple command, control and interface functions, the latter being both interfaces between the user and PRC 10 and the interfaces between the digital electronics/software and the inherently analog devices such as light sources and light detectors. FIG. 15 illustrates system hardware at the block diagram level. It comprises 5 subsystems: an optical bench 500, a microprocessor/controller 600, a user interface 700, a communications module 800, and a power system 900.

As shown in FIG. 15 Optical Bench 500 supports the PRC's illumination and imaging functions. It comprises one or more cameras, such as an ANTcam 350 and a FUNcam 300, and two or more light sources 520, 525, 530, and 535. The camera(s) typically communicate with microprocessor/controller 600 over a standard serial bus. On system power-up, digital initialization commands are sent to the camera(s) to set their operating modes. These commands are stored in volatile memory in the camera(s). Additional commands are sent to the camera(s) during system operation to change operating modes as needed. Video is output over a parallel bus or as a serial, low voltage differential signal (LVDS). Pixel data may be in a raw image format such as DNG, or in processed formats such as Y800. In a preferred embodiment, both ANTcam 505 and FUNcam 510 are used, both are operated in raw image mode. The light sources may be driven in constant current, constant voltage, constant power, or pulsed modes. In a preferred embodiment, all sources are LEDs, and autofocusing light source 450, white light source 410, anterior light source 110, and fixation light source 480 are used. In this preferred embodiment, the sources are all used in constant current mode. In a preferred embodiment, variable optic 310 is the Varioptic, SA variable focus liquid lens model ARCTIC 416™. In another preferred embodiment, variable optic 310 is the Varioptic model A316S variable focus liquid lens with image stabilization. In the latter case, additional control lines between the Microprocessor/Controller 600 and the variable optic 310 are required to drive the steering electrodes of the model A316S liquid lens.

A Microprocessor/Controller Subsystem (MCS) 600 performs the functions of system control and image processing. It also interfaces with human interface devices and telecommunications subsystems.

The core of MCS 600 is a microprocessor 610. In a preferred embodiment, microprocessor 610 is the OMAP35x processor from Texas Instruments (12500 TI Boulevard, P.O. Box 660199, Dallas, Tex. 75266-0199 USA).

Operating software and image data are stored in a memory block 605. In a preferred embodiment, memory 605 comprises non-volatile memory such as RAM.

Microprocessor 610 also communicates video data to a graphics controller 615, which formats it for presentation on a display 705. In a preferred embodiment, the graphics controller 615 also incorporates a touch screen interface, such as the Burr-Brown TSC2003 from Texas Instruments (12500 TI Boulevard, P.O. Box 660199, Dallas, Tex. 75266-0199 USA). This interface is connected to the display 705, receives signals when the user touches the touch screen, and formats these signals as user input to the microprocessor. Graphics controller 615 may also output images to a remote display.

Peripheral interface 620 comprises a chip and one or more firmware drivers. It may be connected to any of a variety of peripheral devices, including computer mice, keyboards, joysticks, trackballs, and graphics tablets. It receives signals from those peripherals, and formats these signals as user input to the microprocessor. In a preferred embodiment, the Peripheral interface 620 comprises the TCA8418 I2C Controlled Keypad Scan IC™ from Texas Instruments (12500 TI Boulevard, P.O. Box 660199, Dallas, Tex. 75266-0199 USA).

Accelerometer 625 comprises a chip and firmware driver. Accelerometer 625 senses the orientation and movement of the device in 3 axes. In a preferred embodiment, model ADXL345BCCZ from Analog Devices (3 Technology Way, Norwood, Mass. 02062, USA) is used to detect lack of movement and provide input to the microprocessor for sleep and hibernate functions that minimize power consumption and maximize battery life. Accelerometer data may also be used to determine PRC 10's orientation, and thus the patient's orientation (e.g., supine, upright) during image capture. This data may be recorded for forensic purposes.

User Interface 700—This subsystem comprises one or more displays and user input devices. Display 705 is a color screen that displays information when PRC 10 is being used, such as patient data, live video images, and stored images, and provides real-time feedback to the user about focus and alignment. In a preferred embodiment, Display 705 is a touch screen AMOLED display, such as the USMP-A43480TP from US Microproducts (6207 Bee Caves Rd, Ste 330, Austin, Tex., 78746, USA) that is incorporated into the device. This display includes a touch screen that provides for user input to the system.

Status indicators 710 comprise discrete devices that convey information to the user about system status such as focus, alignment, and image capture. Status indicators 710 may be visual, audible, and/or tactile. In a preferred embodiment, status indicators 710 are LEDs of various colors located where they are easy for the user to see when operating PRC 10, e.g., adjacent to the display. In another preferred embodiment, status indicators 710 are vibration devices that provide tactile feedback to the user, e.g., vibrate at increasing frequencies as the device becomes more closely aligned or focused.

Peripheral Input Device 720 comprises a computer mouse, keyboard, trackball, graphics tablet, or other user input device. In a preferred embodiment, 720 comprises a compact or folding keyboard connected to PRC 10 via Bluetooth or other wireless protocol that enables rapid entry of data such as patient information.

Voice recognition module 735 enables input to PRC 10 via spoken commands. It comprises a microphone, speech processing chip, and firmware driver. In a preferred embodiment, the speech processing chip is an RSC-4x series speech processor from Sensory, Inc. (575 N. Pastoria Ave., Sunnyvale, Calif., 94085-2916, USA, http://www.sensoryinc.com).

Communication Subsystem 800—This subsystem comprises a number of devices for communicating with external devices and networks.

Cellular module 805 comprises a "cell phone on a chip", firmware driver, and antenna. Cellular module 805 transmits data via a cellular network to a receiving computer where the data may be stored and/or interpreted, and receives data from a transmitting computer via a cellular network. Such received data may include reports, diagnoses, archival images, and annotated images. In a preferred embodiment, cellular module 805 is the GM862 Cellular Quad Band Module™ from Telit Communications S.p.A. (Via Stazione di Prosecco, 5/B, I-34010 Sgonico (Trieste), Italy, http://www.telit.com).

GPS receiver 810 comprises a chip, firmware driver, and antenna. GPS receiver 810 receives satellite signals and computes geographic coordinates. In a preferred embodiment, the Hammerhead™II PMB 2525 GPS receiver from Infineon Technologies AG (C MR, Am Campeon 1-12, 85579 Neubiberg, Germany, http://www.infineon.com) is used, and geographic coordinates at the time of image capture are appended to the image file. This information may be used to establish chain-of-custody of evidence in legal proceedings.

Ethernet controller 820 comprises an Ethernet control chip, firmware driver, and connector such as a female RJ45. In a preferred embodiment, Ethernet controller 820 performs the same functions as cellular module 805, but via a wired Ethernet connection. In a preferred embodiment, Ethernet controller model LAN9220 from Texas Instruments (12500 TI Boulevard, P.O. Box 660199, Dallas, Tex. 75266-0199 USA) is used.

WiFi Module 825 (for wireless data communication) comprises a WiFi interface chip, firmware driver, and antenna. In a preferred embodiment, the WiFi interface chipset WL1251 and WL1251FE, both from Texas Instruments (12500 TI Boulevard, P.O. Box 660199, Dallas, Tex. 75266-0199 USA) is used.

USB controller 830 comprises an serial input/output chip, one or more firmware drivers, and a standard USB connector. USB controller 830 may be used to communicate via USB cable to another computer, to transfer data via a removable USB drive, or to interface to peripheral devices such as computer mice, keyboards, printers or storage devices. In a preferred embodiment, USB Peripheral/Host Controller with SPI Interface™ model MAX3421E from Maxim Integrated Products, Inc. (120 San Gabriel Drive, Sunnyvale, Calif. 94086 USA, http://www.maxim-ic.com) is used.

Modem 835 comprises a modem chip set, firmware driver, and a telephone connector such as a female RJ11. Modem 835 performs the same functions as cellular module 805, but via telephone land lines. In a preferred embodiment, data modem model Si2401 from Silicon Laboratories Inc. (400 West Cesar Chavez, Austin, Tex. 78701 USA, http://www.silabs.com) is used.

Power System—The power system 900 comprises a rechargeable battery, battery charger, mains connection, and switched connection to PRC 10 electronics.

Charger 901 is external to PRC 10. It is connected to mains power by a power cord, and includes a "smart" power source that replenishes battery charge with a current vs. time curve that is optimized for the particular kind of battery that is being used, i.e., achieves reasonable charging times while maximizing the lifetime cycles of the battery. The charger may be connected to PRC 10 via electrical cable. In a preferred embodiment, the charger incorporates a "cradle" for PRC 10 that holds PRC 10 in a stable position and makes electrical contact between the charger and PRC, preferentially by inductive coupling. Inductive coupling eliminates exposed electrical contacts, as well as system failure modes associated with contact degradation or contamination. In another preferred embodiment, the cradle also has locations to charge one or more extra batteries at the same time as PRC 10. In another preferred embodiment, the charger monitors the charging curve to detect the presence of a non-rechargeable (e.g., alkaline) battery and stop charging if a non-rechargeable battery is detected. Charging a non-rechargeable battery can result in electrolyte leakage, heat, and explosion.

Battery 902 provides system power so that PRC 10 can operate without mains connection. Any of the well known battery technologies may be used. In a preferred embodiment, a lithium-ion rechargeable battery is used. In another preferred embodiment, this battery is removable so that a discharged battery can be immediately replaced with a charged one. In another preferred embodiment, non-rechargeable alkaline batteries may be substituted for the lithium-ion battery.

Power button 130 turns the system on and off (not shown in FIG. 15).

Figure 16:
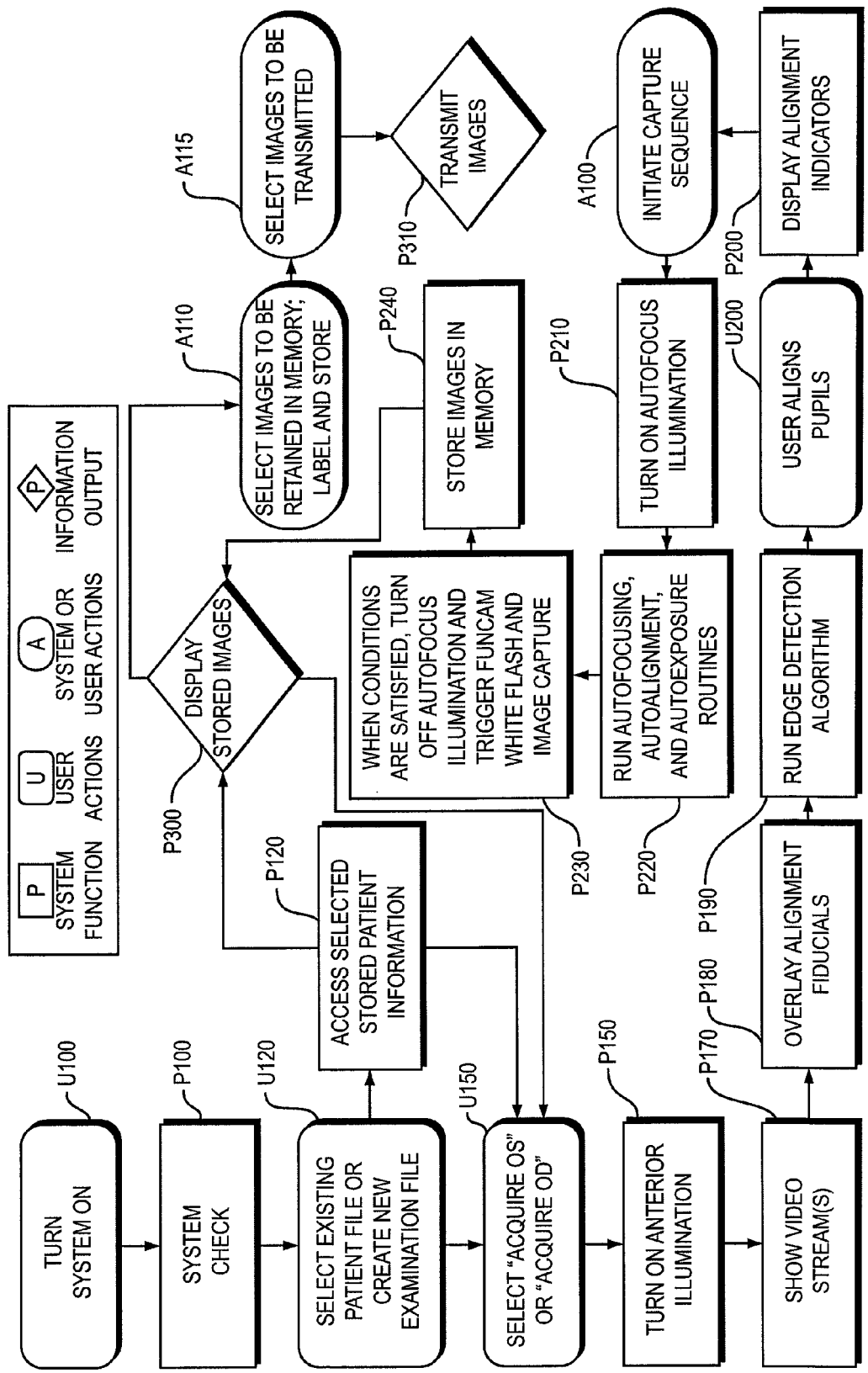
FIG. 16 is a functional flow diagram illustrating an exemplary method of image acquisition.

FUNCTIONAL FLOW DIAGRAM—FIG. 16 illustrates system functions. The key in FIG. 16 shows whether a function is performed by the system, by the user, optionally by either the system or the user, or is just information output.

U100—By pressing power button 130, the user initiates system operation.

P100—PRC 10 performs an automatic system check to ensure that all system hardware is connected and working properly.

U120—The user selects either an existing patient file or creates a new examination file for a new or existing patient. Patient data is input as needed using integrated or peripheral human input devices. In a preferred embodiment, the input devices comprise a touch screen 705 and voice recognition module 735.

P120—If an existing patient file is selected, any files stored in memory 605 are accessed.

P300—Accessed files are viewed on display 705, on a peripheral display via USB controller 825, or on another computer via NIC 820.

U150—If a new examination is to be performed, the user selects either the left eye (OS) or right eye (OD).

P150—In the preferred embodiment, the system is equipped with both FUNcam and ANTcam. If the ANTcam is present, the system activates the anterior illuminator.

P170—A live video stream from the FUNcam is displayed. In the preferred embodiment, live video from the ANTcam is displayed in another part of the screen at the same time as the FUNcam video stream. An alternative embodiment is to use a picture-in-picture arrangement, where one video stream occupies most or all of the screen, and the second video stream is overlaid or inset on part of the screen.

P180—Alignment fiducials are overlaid on the FUNcam video stream. Exemplary fiducials are crosshairs, boxes, and/or cursors. In a preferred embodiment, the fiducials are one or more concentric circles, overlaid onto both the ANTcam and FUNcam video streams.

P190/U200/P200—In the preferred embodiment, the system is continuously performing image processing on the ANTcam video stream. As the user brings PRC 10 close to the patient's eye, an edge detecting routine determines the location of the patient's pupil relative to the alignment fiducials. In the preferred embodiment, cvCopyMakeBorder, cvCanny, and cvThreshold functions from the open source OpenCV image processing library are used to detect the edge of the patient's pupil, or segments of it. ROIs may be used to increase the frame rate of ANTcam 305 to provide faster feedback. In an preferred embodiment, four square ROIs are placed to intersect four quadrants of the pupil edge. Factors relating to these edge segments, such as their centroid, are then calculated, and the centroid location is compared to the origin of the fiducials. To guide alignment, visual, audible, and/or tactile feedback are communicated to the user as a shift vector. In a preferred embodiment, alignment indicators are shown on Display 705 that communicate to the user in which direction and how far PRC 10 must be moved to achieve alignment of the edge centroid with the fiducial origin. Exemplary indicators include crosshairs, boxes, and/or cursors. In a preferred embodiment, the indicators are arrows pointing in the direction that PRC 10 should be moved, with the length of the arrows representative of the magnitude of required movement (shift vector).

The system determines coarse focus (i.e., alignment in the Z axis, toward/away from the patient's eye) by also using the edge detection described above. In a preferred embodiment, the ANTcam's objective lens is designed to have a short depth of field. A sharp image of the anterior of the eye (edge of pupil, iris) will therefore be achieved only when PRC 10 is the correct distance from the patient's pupil, plus or minus a small amount. By continuously determining the sharpness of the edge of the patient's pupil, and monitoring trends in sharpness as PRC 10 is moved, the system can determine both degree of focus and direction along the Z-axis in which PRC 10 should be moved. These two pieces of information are communicated to the user with visual, audible, and/or tactile feedback. In a preferred embodiment, state of focus is indicated on display 705 by a line digitally overlaid on the edge of the patient's pupil. The width of the line corresponds to the "softness" of the edge of the pupil. When the edge is soft (out of focus), the line is wide. When the edge is in sharp focus the line becomes very narrow. This method "amplifies" the user's ability to visually detect edge sharpness. If PRC 10 needs to be moved closer to the patient, an arrow shown in perspective view points towards the eye. If PRC 10 needs to be move away, an arrow shown in perspective view points away from the eye.

Tilt of PRC 10 relative to the optical axis of the eye is also determined using edge detection of the pupil. When the user is looking at the central fixation target (i.e., along PRC 10's optical axis), the entire pupil will have the same state of focus. If PRC 10 is tilted, there will be differential focus on parts of the pupil. This is represented by showing an incomplete overlaid circle. The user then re-instructs the patient to look at the fixation target.

A100—Image capture sequence is initiated. The user may initiate capture by pressing a button, touching the touch screen, or issuing a voice command. In the preferred embodiment, the system is configured to initiate automatically when all pre-conditions are satisfied.

P210—The system turns on the autofocus illumination. In the preferred embodiment, this illumination is fixed at a level that is comfortable for patients.

P220—In previous steps, in the preferred embodiment, the system processed ANTcam images to achieve "coarse alignment" and "coarse focus". In step 220, the system processes the FUNcam video stream to achieve fine focus and alignment, as well as autoexposure. Fine autofocus is achieved by continuously performing image processing of the FUNcam video stream to determine the focus state of structures in the retina. Structures include vasculature, nerves, and the optic cup. Autofocus may be performed by computing frequency histograms. Histograms containing more high frequency components have more detail, i.e., better focus. In a preferred embodiment, state of focus is determined with the OpenCV contrast histogram function cvContrastHistogram. After determining the contrast of an initial video frame (#1), variable power optical element 310 is automatically stepped in direction A (e.g., more optical power), and the contrast of frame 2 is determined. If the contrast improved from frame 1 to frame 2, the variable power optical element 310 is stepped in the same direction for each subsequent frame until contrast stops increasing or begins to decrease. Best focus is achieved when small adjustments of the variable power optical element in either direction result in a decrease in contrast. If the contrast decreased from frame 1 to 2, then the variable power optical element is changed in direction B (e.g., less optical power), and the iteration is repeated in the same direction until contrast stops increasing or begins to decrease. Furthermore, in a preferred embodiment, to achieve faster convergence on the best focus, the magnitude of the adjustments of the variable power optical element is intelligently varied depending on the frame to frame changes in focus. With this approach, adjustments tend to be initially large and become smaller as best focus is achieved. In a further preferred embodiment, the shift vectors calculated in steps P190/U200/P200 are used to determine the correct voltage to be applied to specific electrodes on variable optic 310 (Varioptic liquid lens model A316S) to compensate for the shift vector. This differential voltage, applied to the electrodes, very rapidly corrects the image shift caused by inadvertent movement, i.e., returns the image to it's prior location on the FUNcam image sensor 342. Because the frame rate of ANTcam 350 can be so high compared to the frame rate of FUNcam 300, image shifts can be corrected during a single FUNcam 300 exposure, eliminating or minimizing the effects of motion blur, and improving the sharpness of captured images.

Because PRC 10 must illuminate and image the retina through patient pupils as small as 2 mm, precise alignment in X or Y axes is essential. Autoalignment is achieved by detecting artifacts in the FUNcam video images that result from misalignment in these axes between the illumination and/or imaging pupils, and the patient's pupil. In a preferred embodiment, artifacts such as non-uniformity of the retinal image are used to detect misalignment. When alignment in X and Y axes is good, luminance values at all field points generally fall within a fairly narrow range. When alignment in X or Y is inadequate, parts of the image are too dark or too light. These image artifacts are detected with image processing by sampling regions of interest (ROIs) at a variety of pre-determined field points, particularly around the field edges, calculating a mean luminance value for each ROI, and calculating standard deviations of luminance values between the ROIs. The effects on the calculation of retinal structures such as vasculature, nerves, and exudates are eliminated by defining blobs within each ROI edge using the thresholding and edge detection functions described above, and then using OpenCV's cvErode and cvDilate image processing functions. These two functions remove blobs representing fine features in the ROIs, leaving for analysis only larger remaining blobs, i.e., areas of the retina in-between the fine structures. To guide alignment, visual, audible, and/or tactile feedback are communicated to the user. In a preferred embodiment, alignment indicators on Display 705 show the user which way to move PRC 10 to maximize the sum of luminance value of all the ROIs while minimizing standard deviation between the ROIs. Exemplary indicators include crosshairs, boxes, and/or cursors. In a preferred embodiment, the indicators are arrows pointing in the direction that PRC 10 should be moved to achieve alignment. When pre-set ranges for the means and standard deviations of luminances for these blobs are satisfied, autoalignment criteria are satisfied.

Autoexposure is required because the reflectance, or albedo, of the retina varies from eye to eye. It is therefore desirable to adjust sensor integration time and/or illumination level during image capture to obtain optimally exposed images. In a preferred embodiment, autoexposure is achieved by using the results of the autoalignment computations to adjust the sensor's integration time and/or the power of the white LED during image capture. Because the illumination used during autofocus/autoalignment is at a fixed level, if the albedo of the patient's retina is low or high, the average or sum luminance value of the blobs that was computed when autoalignment was achieved will be low or high, respectively. The ratio of the average or sum luminance relative to a known nominal is used to adjust the sensor integration time or white LED power during image capture.

P230—When pre-set conditions for focus and alignment are satisfied, and the correct exposure is calculated, the system automatically turns off the autofocus illumination, turns on the white illumination, and captures a burst of images, i.e., a short video clip. In a preferred embodiment, images are captured at a rate of at least 30 frames per second for a period of at least 200 ms. Furthermore, in a preferred embodiment, "autobracketing" is used to further ensure that at least one good image per burst is captured. Autobracketing means capturing images at the nominal calculated exposure, as well as at exposures below and above the nominal, e.g., ±½ f-stop, ±1 f-stop, etc. Still further, in a preferred embodiment, initiation of the white illumination and image capture burst are slightly delayed after the autofocusing illumination is turned off. During this period when no illumination is present, the patient's pupil relaxes (dilates), which makes lateral alignment of PRC 10 to the patient's pupil less sensitive and improves the likelihood of good images being captured.

P240—Images are stored in memory and are immediately available for viewing.

P300—The user inputs commands to display the saved images on the integrated display 705, on a peripheral display, or on another computer. In an alternative embodiment, the system automatically displays the images on display 705 as well as any peripheral display or computer for which a connection is detected.

A110—The user reviews captured images and selects which ones to keep and which ones to discard. The user then labels and stores the selected images in memory 605. In an alternative embodiment, the system uses image qualification routines to select images that meet pre-set criteria for focus, alignment, and exposure. The same image processing routines used for autofocus, autoalignment, and autoexposure (described above) are used to determine whether images saved to memory satisfy pre-set criteria. After qualification, images are be labeled and stored using user-defined naming defaults. If no good images have been captured, the user returns to step U150.

A115—The user selects images to be transmitted to another memory device or telecommunications network.

P310—The system completes the transmission.

Method of acquiring images—The portable retinal camera also comprises a method of acquiring retinal images. In general terms, the method comprises the steps of performing a coarse alignment by manually positioning the portable camera in front of the patient's eye, usually aided by a pupil image display and image processing software in the PRC. Once coarse alignment is achieved, the retina is illuminated with deep red light and the imaging camera collects images of the retina that are processed by autoexposure and autofocus image processing modules. Based on the signals from these modules, a variable power optical element is driven to achieve best focus and the camera timing parameters are adjusted for nominally best exposure. Once focus and exposure are set, the retina is illuminated with white light and one or more full color images of the retina are captured. Additional steps may be added to this method; for example, a fixation target may be displayed to the patient to help stabilize the retinal position during coarse and fine alignment.

In more detail, the method of acquiring portable retinal camera images comprises the steps of:

1) Aligning a portable retinal camera to a patient's eye, optionally using a real-time video stream from a sensor co-aligned with the primary image sensor;
2) Optionally processing the video stream to generate alignment estimates and displaying the results;
3) Initiating, manually or automatically, a pre-determined image acquisition sequence after coarse alignment is achieved;
4) Illuminating the patient's retina with a deep red or near IR illuminator;
5) Collecting a real-time image stream from a retinal camera and processing said stream to adjust the camera's exposure parameters;
6) Further processing said stream to estimate focus error and adjusting the optical focusing power of a variable power optical element to achieve best focus in said camera.
7) Initiating the capture of a series of retinal images upon achieving focus and exposure settings, wherein the step of initiating further comprises the steps of:
    a) Activating a white light illumination source, said source directed to the retina;
    b) Retrieving a pre-planned sequence of desired image capture conditions;
8) Implementing said pre-planned sequence of desired image capture conditions;
9) Ending the capture sequence by de-activating the white light source;
10) Storing, processing, and/or displaying one or more captured images.

One of ordinary skill in the art of optical engineering will recognize that the specific order or location of certain of the above described optical elements is for convenience and explanation only and is not intended to be limiting. For example, the function of polarizer 227 is not impaired if it is placed between objective 207B and beamsplitter/Fold mirror 230A/B instead of between objective 207B and beam combiner 495.

What is claimed is:

1. A camera for capturing an image of an object, comprising:
    a first light source;
    a second light source;
    an image-sensing system comprising at least a first image sensor;
    a multiple branch optical system that transmits outgoing light from the first and second light sources to the object, and transmits incoming light from the object to the image-sensing system, the multiple branch optical system comprising an autofocusing element that varies the focus of the incoming light;
    an image display;
    a controller that controls the operation of the first and second light sources, controls acquisition of images by the image-sensing system, and controls the display of images on the image display, the controller activating the first light source and using the resulting captured image to automatically adjust the image exposure parameters and automatically adjust the variable power optical element to improve the image focus, and the controller then activating the second light source and acquiring one or more images of the object while the second light source is activated; and
    a closed loop control system having image shift as an input, where the control system determines the magnitude and direction of frame shift from a nominal center and generates a control signal that is used to modify the optical system to move the image back toward the nominal center.

2. The camera of claim 1 wherein the controller further causes an acquired image to be displayed on the image display to allow coarse alignment of the camera with the object.

3. The camera of claim 1 wherein the image-sensing system further comprises a second image sensor, wherein at least one of said two image sensors is a high-resolution color sensor.

4. The camera of claim 3 wherein the multiple branch optical system defines a first light path from the first light source to the object, a second light path from the second light source to the object, a third light path from the object to the first image sensor and a fourth light path from the object to the second image sensor, where none of the light paths are entirely coincident.

5. The camera of claim 3 wherein the controller further accomplishes image stabilization using one image sensor running at a high frame rate to provide real-time image stabilization feedback to a second image sensor with a lower frame rate and relatively long exposures.

6. The camera of claim 1 wherein the first light source emits deep red or near infrared light.

7. The camera of claim 6 wherein the first light source comprises one or more LEDs.

8. The camera of claim 1 wherein the second light source comprises one or more LEDs that emit broadband visible light.

9. The camera of claim 1 wherein the object is the fundus of an eye.

10. The camera of claim 9 wherein the optical system separates the illumination and imaging light paths such that these two light paths do not overlap in the pupil plane of the eye.

11. The camera of claim 9 wherein the optical system comprises configurable masks to control how one or both of the illumination and the image light is passed through the pupil of the eye.

12. The camera of claim 1 wherein the autofocusing element comprises an electro-optical lens with variable focal length, wherein the focal length is varied by varying a voltage applied to the lens.

13. The camera of claim 1 further comprising a third light source.

14. The camera of claim 13 wherein the third light source illuminates the object directly without elements of the multiple branch optical system between the third light source and the object.

15. The camera of claim 14 further comprising a hand-held housing that contains the first and second light sources, the image sensor, the multiple branch optical system and the controller, wherein the image display is mounted to the housing so as to be visible from the outside, wherein the housing defines an image acquisition aperture on a patient-facing side of the housing through which the light from the first and second light sources passes and light from the eye passes to reach the image-sensing system, and wherein the third light source is mounted on the outside of the patient-facing side of the housing proximate the image acquisition aperture.

16. The camera of claim 13 wherein the third light source emits near infrared light.

17. The camera of claim 16 wherein the first light source emits deep red or near infrared light that is used by the controller to accomplish automatic focus, the second light source comprises an LED that emits broadband visible light that is used to capture a high-resolution image of light that is diffusely reflected by the fundus, and the light from the third light source is used by the controller to assist with coarse image alignment.

18. The camera of claim 1 wherein the optical system further comprises a polarizer for polarizing the light from at least one of the first and second light sources, and a polarizing beamsplitter for directing to an imaging sensor the orthogonally polarized component of the polarized light that is diffusely reflected from the object.

19. The camera of claim 18 wherein the optical system further comprises a light beam combiner that directs the light from the first and second light sources along substantially the same light path.

20. The camera of claim 1 further comprising a data communication system that transmits image data from the camera or receives data.

21. The camera of claim 1 wherein the controller assists with coarse image alignment using a focus estimation image processing algorithm that calculates a focus figure-of-merit and notifies the operator when the figure-of-merit exceeds a predetermined threshold.

22. The camera of claim 1 wherein the variable power optical element comprises an electro-optical lens with variable focal length, wherein the focal length is varied by varying a voltage applied to the lens, and wherein the control signal comprises a differential voltage that is applied to the electro-optical lens.

23. The camera of claim 1 wherein the multiple branch optical system comprises an electronically-variable aperture stop in the path of incoming light to an image sensor, and the controller further controls the stop size to improve focus during coarse image alignment.

24. The camera of claim 1 further comprising at least one of a GPS receiver that indicates the location at which an image is captured and a device for determining the orientation of the camera when an image is captured.

25. The camera of claim 24 wherein the controller associates with an image any or all of the time an image was captured, the location where it was captured, and the orientation of the camera when it was captured.

26. A camera for capturing an image of the fundus of a human eye, comprising:
  a first light source that emits deep red or near infrared light;
  a second light source that comprises an LED that emits broadband visible light that is used to capture a high-resolution image of light that is diffusely reflected by the fundus;
  a third light source that emits near infrared light;
  a fixation target illuminator system comprising an optical projector with a fixation target light source, the fixation target illuminator system presenting a virtual image of a target to the eye, and further comprising a variable focus element in the fixation target light path to vary the apparent distance of the virtual image of the fixation target light source from the eye;
  an image-sensing system comprising a first image sensor and a second image sensor that is a color sensor of high resolution;
  a multiple branch optical system that transmits outgoing light from the first and second light sources to the eye and transmits incoming light from the eye to the image-sensing system, and defines a first light path from the first light source to the eye, a second light path from the second light source to the eye, a third light path from the eye to the first image sensor, a fourth light path from the eye to the second image sensor, and a fixation target light path from the fixation target light source to the eye, the multiple branch optical system comprising an electro-optical lens that effects a change in its focal length, to vary the focus of the incoming light to the second image sensor, wherein the focal length is varied by varying a voltage applied to the lens, the optical system further comprising a polarizer for polarizing the light from the second light source, a polarizing beamsplitter for directing to the second image sensor the orthogonally polarized component of the polarized light that is diffusely reflected from the fundus, and a light beam combiner that directs the light from the first and second light sources along substantially the same light path, wherein the optical system separates the illumination and imaging light paths such that these two light paths do not overlap in the pupil plane of the eye;
  an image display;
  a controller that controls the operation of the first, second and third light sources, controls the fixation target illuminator system, controls acquisition of images by the image-sensing system, and controls the display of images on the image display, the controller causing an acquired image to be displayed on the image display to allow coarse alignment of the camera with the eye, activating the first light source and using the resulting captured image to automatically adjust the image exposure parameters and automatically adjust the variable power optical element to improve the image focus, and the controller then activating the second light source and acquiring one or more images of the fundus while the second light source is activated, wherein the light from the third light source is used by the controller to assist with coarse image alignment using a focus estimation image processing algorithm that calculates a focus figure-of-merit and notifies the operator when the figure-of-merit exceeds a predetermined threshold;
  a data communication system that transmits image data from the camera or receives data; and a hand-held housing that contains the first and second light sources, the fixation target illuminator system, the image sensor, the multiple branch optical system and the controller, wherein the image display is mounted to the housing so as to be visible from the outside, wherein the housing defines an image acquisition aperture on a patient-facing side of the housing through which the light from the first and second light sources passes and light from the eye passes to reach the image-sensing system, and wherein the third light source is mounted on the outside of the patient-facing side of the housing proximate the image acquisition aperture.

27. A method of capturing an image of the fundus of the eye, comprising:
(i) providing a camera comprising:
a first light source that emits deep red or near infrared light;
a second light source that comprises an LED that emits broadband visible light that is used to capture a high-resolution image of light that is diffusely reflected by the fundus;
a third light source that emits near infrared light;
a fixation target illuminator system comprising an optical projector with a fixation target light source, the fixation target illuminator system presenting a virtual image of a target to the eye, and further comprising a variable focus element in the fixation target light path to vary the apparent distance of the virtual image of the fixation target light source from the eye;
an image-sensing system comprising a first image sensor and a second image sensor that is a color sensor of high resolution;
a multiple branch optical system that transmits outgoing light from the first and second light sources to the eye and transmits incoming light from the eye to the image-sensing system, and defines a first light path from the first light source to the eye, a second light path from the second light source to the eye, a third light path from the eye to the first image sensor, a fourth light path from the eye to the second image sensor, and a fixation target light path from the fixation target light source to the eye, the multiple branch optical system comprising an electro-optical lens that effects a change in its focal length, to vary the focus of the incoming light to the second image sensor, wherein the focal length is varied by varying a voltage applied to the lens, the optical system further comprising a polarizer for polarizing the light from the second light source, a polarizing beamsplitter for directing to the second image sensor the orthogonally polarized component of the polarized light that is diffusely reflected from the fundus, and a light beam combiner that directs the light from the first and second light sources along substantially the same light path, wherein the optical system separates the illumination and imaging light paths such that these two light paths do not overlap in the pupil plane of the eye;
an image display;
a controller that controls the operation of the first, second and third light sources, controls the fixation target illuminator system, controls acquisition of images by the image-sensing system, and controls the display of images on the image display;
a data communication system that transmits image data from the camera or receives data; and
a hand-held housing that contains the first and second light sources, the fixation target illuminator system, the image sensor, the multiple branch optical system and the controller, wherein the image display is mounted to the housing so as to be visible from the outside, wherein the housing defines an image acquisition aperture on a patient-facing side of the housing through which the light from the first and second light sources passes and light from the eye passes to reach the image-sensing system, and wherein the third light source is mounted on the outside of the patient-facing side of the housing proximate the image acquisition aperture; and
(ii) operating the controller to first activate the third light source and cause an acquired image to be displayed on the image display to allow coarse alignment of the camera with the eye, and assist with coarse alignment using a focus estimation image processing algorithm that calculates a focus figure-of-merit and notifies the operator when the figure-of-merit exceeds a predetermined threshold, then activate the first light source and use the resulting captured image to automatically adjust the image exposure parameters and automatically adjust the autofocusing element to improve the image focus, and the controller then activating the second light source and acquiring one or more images of the fundus while the second light source is activated.

28. A camera for capturing an image of the fundus of an eye, comprising:
a first light source;
a second light source;
a fixation target illuminator system comprising an optical projector with a fixation target light source, the fixation target illuminator system presenting a virtual image of a target to the eye, wherein the fixation target illumination source comprises a plurality of point light sources, one defining a center and others arranged at a variety of field points relative to the center and wherein the fixation target light source is selected from the group of light sources including: one or more point sources; an extended object; and an electro-optic display device;
an image-sensing system comprising at least a first image sensor;
a multiple branch optical system that transmits outgoing light from the first and second light sources to the object, and transmits incoming light from the object to the image-sensing system, the multiple branch optical system comprising an autofocusing element that varies the focus of the incoming light;
an image display; and
a controller that controls the operation of the first and second light sources, controls acquisition of images by the image-sensing system, and controls the display of images on the image display, the controller activating the first light source and using the resulting captured image to automatically adjust the image exposure parameters and automatically adjust the variable power optical element to improve the image focus, and the controller then activating the second light source and acquiring one or more images of the object while the second light source is activated.

29. The camera of claim 28 wherein the multiple branch optical system defines a fixation target light path from the fixation target light source to the eye.

30. The camera of claim 29 wherein the fixation target illuminator system further comprises a variable focus element in the fixation target light path, to vary the apparent distance of the virtual image of the fixation target light source from the eye.

31. The camera of claim 30 wherein the variable focus element is electro-mechanically adjusted.

* * * * *